(12) United States Patent
Okubo et al.

(10) Patent No.: US 8,894,932 B2
(45) Date of Patent: Nov. 25, 2014

(54) REAGENT PREPARING DEVICE AND SPECIMEN PROCESSING SYSTEM

(75) Inventors: Koichi Okubo, Kobe (JP); Noriyuki Nakanishi, Kakogawa (JP); Masahiko Oguro, Kobe (JP); Tomoyuki Asahara, Kobe (JP); Takayuki Nakajima, Nishinomiya (JP)

(73) Assignee: Sysmex Corporation, Kobe (JP)

( * ) Notice: Subject to any disclaimer, the term of this patent is extended or adjusted under 35 U.S.C. 154(b) by 779 days.

(21) Appl. No.: 12/732,964

(22) Filed: Mar. 26, 2010

(65) Prior Publication Data

US 2010/0247383 A1  Sep. 30, 2010

(30) Foreign Application Priority Data

Mar. 30, 2009  (JP) ................................. 2009-081283

(51) Int. Cl.

| | |
|---|---|
| *G01N 35/10* | (2006.01) |
| *G01N 1/38* | (2006.01) |
| *G01N 27/06* | (2006.01) |
| *G01N 35/00* | (2006.01) |

(52) U.S. Cl.
CPC .......... *G01N 27/06* (2013.01); *G01N 35/00693* (2013.01); *G01N 35/00594* (2013.01); *G01N 2035/00673* (2013.01)
USPC ................................ 422/76; 422/67; 436/179

(58) Field of Classification Search
CPC ............ G01N 27/06; G01N 35/00693; G01N 35/00594; G01N 2035/00679
See application file for complete search history.

(56) References Cited

U.S. PATENT DOCUMENTS

| | | | |
|---|---|---|---|
| 4,678,755 A * | 7/1987 | Shinohara et al. ............... | 436/43 |
| 5,800,056 A | 9/1998 | Suzuki et al. | |
| 5,888,823 A | 3/1999 | Matsumoto et al. | |
| 2007/0212261 A1 | 9/2007 | Tanaka et al. | |
| 2010/0161243 A1 * | 6/2010 | Nagai et al. ...................... | 702/25 |
| 2010/0292944 A1 * | 11/2010 | Howell et al. .................... | 702/65 |
| 2011/0223077 A1 | 9/2011 | Tanaka et al. | |

FOREIGN PATENT DOCUMENTS

| | | |
|---|---|---|
| JP | 2003-294663 A | 10/2003 |
| JP | 2005-069956 A | 3/2005 |
| JP | 2007-240430 A | 9/2007 |
| JP | 2008-046144 A | 2/2008 |
| WO | WO2008068484 * | 6/2008 |
| WO | WO 2009/031461 A1 | 3/2009 |

* cited by examiner

*Primary Examiner* — P. Kathryn Wright
(74) *Attorney, Agent, or Firm* — Brinks Gilson & Lione

(57) ABSTRACT

A reagent preparing device capable of supplying a predetermined reagent, which includes a first liquid and a second liquid different from the first liquid, to a measurement section for measuring a specimen using the reagent, comprising: a reagent preparing section for preparing the predetermined reagent; a characteristic measurement device for measuring characteristic of the reagent prepared by the reagent preparing section; and a controller configured for performing operations comprising, controlling the supply of reagent prepared by the reagent preparing section to the measurement section according to the measurement result by the characteristic measurement device, and calibrating the characteristic measurement device based on a known characteristic value of a standard liquid having the known characteristic value and a measurement result obtained by measuring the characteristic of the standard liquid by the characteristic measurement device, is disclosed. A specimen processing system is also disclosed.

16 Claims, 22 Drawing Sheets

REAGENT PREPARING DEVICE AND SPECIMEN PROCESSING SYSTEM

RELATED APPLICATIONS

This application claims priority under 35 U.S.C. §119 to Japanese Patent Application No. 2009-081283 filed on Mar. 30, 2009, the entire content of which is hereby incorporated by reference.

BACKGROUND OF THE INVENTION

1. Field of the Invention

The present invention relates to reagent preparing devices and specimen processing systems, and in particular, to a reagent preparing device capable of preparing a reagent from a plurality of different liquids, and a specimen processing system.

2. Description of the Related Art

Conventionally, a reagent preparing device capable of preparing a reagent from a plurality of different liquids is known (see e.g., U.S. Pat. No. 5,800,056). In U.S. Pat. No. 5,800,056, the reagent used in a measurement section is automatically prepared from high concentration reagent and pure water. The reagent preparing device described in U.S. Pat. No. 5,800,056 includes a reagent quantifying tank for accommodating a high concentration reagent, and a pure water quantifying tank for accommodating pure water. The reagent preparing device further includes a preparing tank, connected to the reagent quantifying tank and the pure water quantifying tank, for preparing the reagent inside, a storage tank, connected to the preparing tank, for accommodating the reagent prepared in the preparing tank, and a supply tank, connected to the storage tank, for accommodating the reagent waiting to be supplied to the measurement section. In U.S. Pat. No. 5,800,056, a concentration sensor including an electrical conductivity meter is arranged in the preparing tank, and the preparation of the reagent is completed assuming the reagent of the desired concentration is obtained when the electrical conductivity of the reagent is within a desired range.

The reagent prepared by the reagent preparing device described in U.S. Pat. No. 5,800,056 is used to measure the specimen in the measurement section including a flow cytometer. The flow cytometer is calibrated using a standard liquid described in U.S. Pat. No. 5,888,823 and the like so as to obtain an accurate measurement value.

However, even if the measurement section is appropriately calibrated, an accurate measurement value may not be obtained in the measurement section if the quality of the reagent supplied from the reagent preparing device to the measurement section is lowered. For instance, in the reagent preparing device described in U.S. Pat. No. 5,800,056, the reagent is supplied to the measurement section only when confirmed that a desired concentration is obtained by the concentration sensor, and thus the concentration of the reagent to be supplied is normally constant. However, if the electrical conductivity output by the electrical conductivity meter is deviated from the true value, the reagent of low quality having a concentration different from the desired concentration may be supplied to the measurement section although the reagent of the desired concentration is actually not obtained. The analysis result of the specimen measured using such reagent of low quality has low reliability, and a need to replace the reagent and perform the measurement again arises.

SUMMARY OF THE INVENTION

The scope of the present invention is defined solely by the appended claims, and is not affected to any degree by the statements within this summary.

A first aspect of the present invention is a reagent preparing device capable of supplying a predetermined reagent, which includes a first liquid and a second liquid different from the first liquid, to a measurement section for measuring a specimen using the reagent, comprising: a reagent preparing section for preparing the predetermined reagent; a characteristic measurement device for measuring characteristic of the reagent prepared by the reagent preparing section; and a controller configured for performing operations comprising, controlling the supply of reagent prepared by the reagent preparing section to the measurement section according to the measurement result by the characteristic measurement device, and calibrating the characteristic measurement device based on a known characteristic value of a standard liquid having the known characteristic value and a measurement result obtained by measuring the characteristic of the standard liquid by the characteristic measurement device.

A second aspect of the present invention is a specimen processing system comprising: a measurement section for measuring a specimen using a predetermined reagent including a first liquid and a second liquid different from the first liquid; a reagent preparing section for preparing the predetermined reagent to be supplied to the measurement section; a characteristic measurement device for measuring characteristic of the reagent prepared by the reagent preparing section; and a controller configured for performing operations comprising, controlling supply of reagent prepared by the reagent preparing section to the measurement section according to the measurement result by the characteristic measurement device, and calibrating the characteristic measurement device based on a known characteristic value of a standard liquid having the known characteristic value and a measurement result obtained by measuring the characteristic of the standard liquid by the characteristic measurement device.

DETAILED DESCRIPTION OF THE PREFERRED EMBODIMENTS

The preferred embodiments of the present invention will be described hereinafter with reference to the drawings.

First Embodiment

First, the configuration of the reagent preparing device according to the first embodiment of the present invention will be described with reference to FIGS. 1 to 10. In the first embodiment, a case of using the reagent preparing device 4 according to the first embodiment of the present invention as one part of a blood analyzer 1 for performing a blood test will be described.

Figure 1:
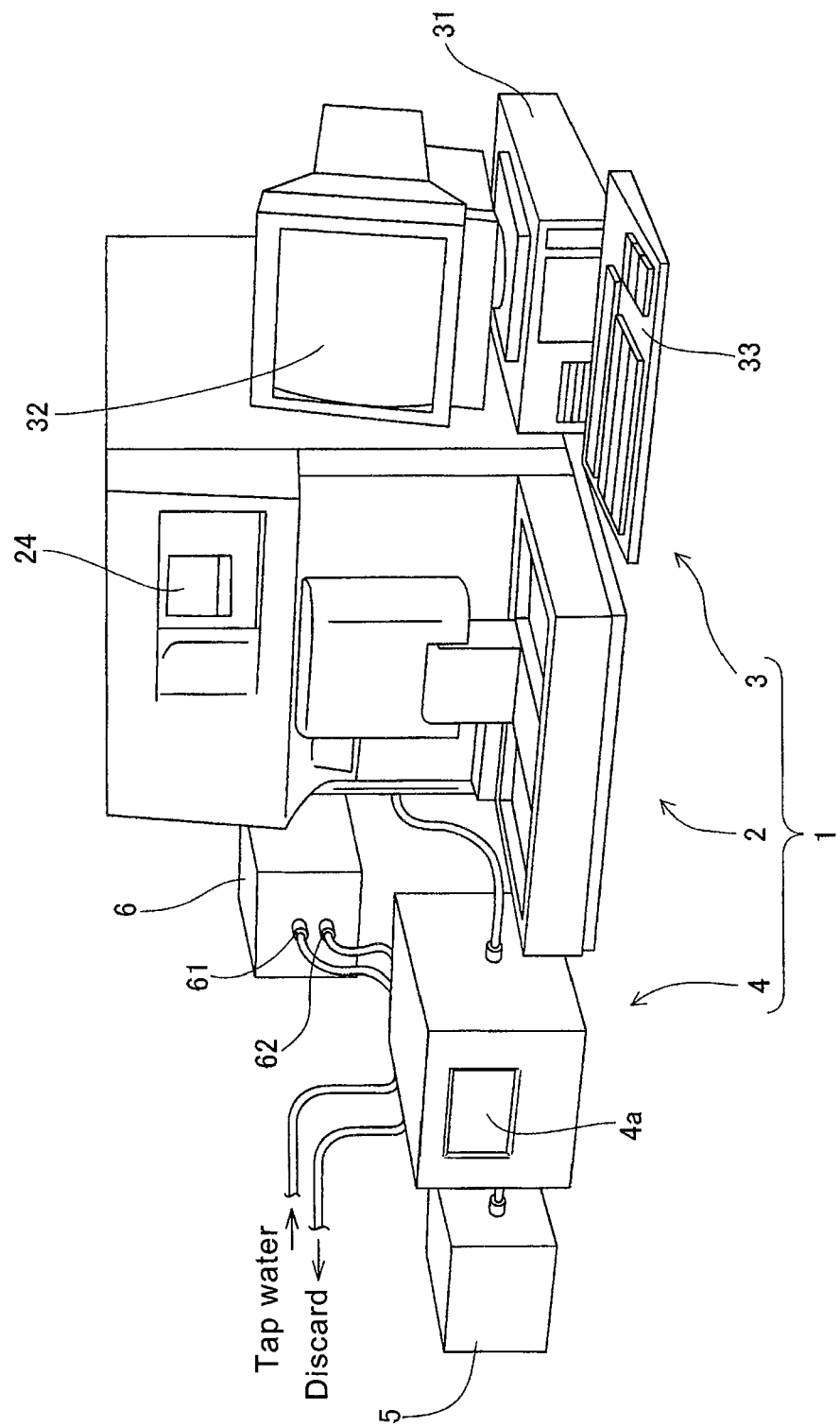
FIG. 1 is a perspective view showing a usage state of a reagent preparing device according to a first embodiment of the present invention.

As shown in FIG. 1, the blood analyzer 1 is configured by the measurement section 2 having a function of measuring blood, the data processing section 3 for analyzing the measurement data output from the measurement section 2 and obtaining an analysis result, and the reagent preparing device 4 for preparing a reagent to be used in the processing of specimens. The measurement section 2 is configured to perform measurements on red blood cells, white blood cells, reticulycytes, and blood platelets in the blood through a flow cytometry method. The measurement section 2 is configured to dilute the blood using a reagent prepared and supplied by the reagent preparing device 4 and to perform measurements on red blood cells, white blood cells, reticulocyte, and blood platelets. The measurement section 2 is also configured to clean a sampling valve 21b, a reaction chamber 21c (see FIG. 3), and the like arranged in a sample preparing unit 21, as well as a sheath flow cell 22c (see FIG. 4), and the like arranged in a detection unit 22, which are to be hereinafter described, using the reagent prepared and supplied by the reagent preparing device 4 as a cleaning fluid. The flow cytometry method is a measurement method of particles (blood cells) for detecting the forward scattered light, the lateral scattered light, and the lateral fluorescence emitted by the particles (blood cells) in the measurement sample by forming a sample flow including the measurement sample and irradiating the sample flow with laser light.

Figure 2:
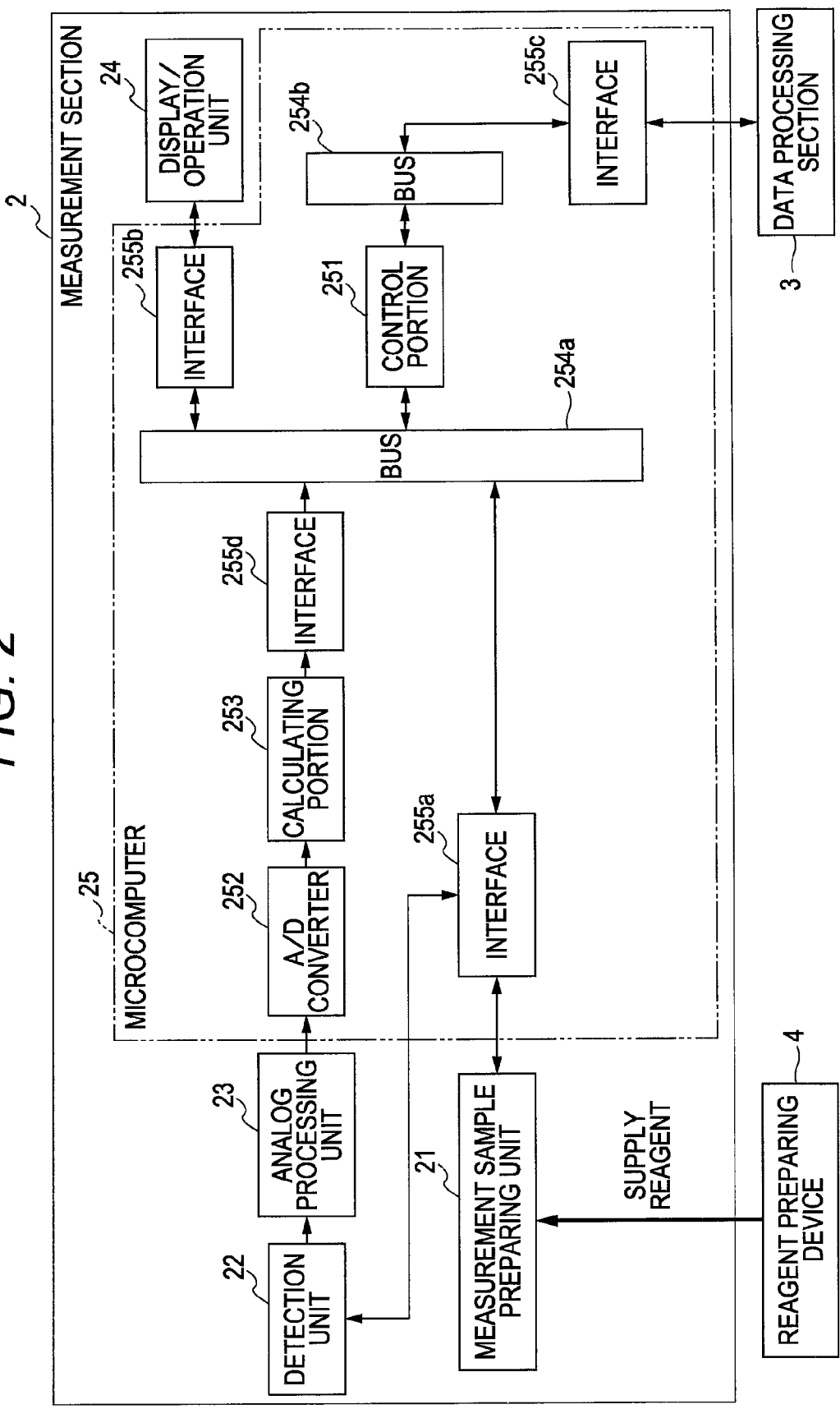
FIG. 2 is a block diagram showing a configuration of a blood analyzer including the reagent preparing device according to the first embodiment shown in FIG. 1.

As shown in FIG. 2, the measurement section 2 includes a measurement sample preparing unit 21, a detection unit 22 for performing a measurement of the measurement sample, an analog processing unit 23 with respect to the output of the detection unit 22, a display/operation unit 24, and a microcomputer 25 for controlling the measurement section 2.

Figure 3:
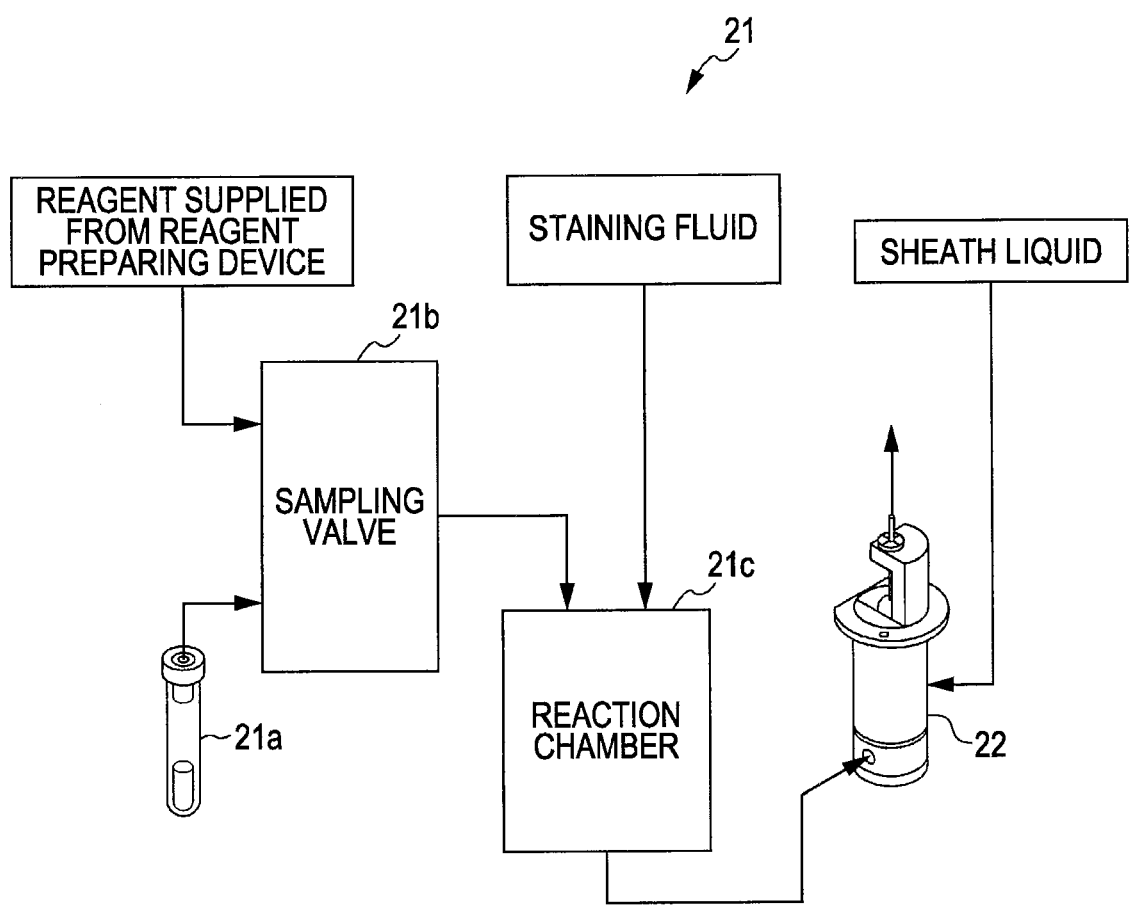
FIG. 3 is a view explaining a sample preparing unit of the blood analyzer including the reagent preparing device according to the first embodiment shown in FIG. 1.

The measurement sample preparing unit 21 is arranged to prepare a white blood cell measurement sample, a reticulocyte measurement sample, and a blood platelet measurement sample. As shown in FIG. 3, the measurement sample preparing unit 21 includes the sampling valve 21b for aspirating blood and the reaction chamber 21c. A blood collecting tube 21a stores the blood to be analyzed.

The sampling valve 21b has a function of quantifying the blood of the blood collecting tube 21a aspirated by an aspiration pipette (not shown) by a predetermined amount. The sampling valve 21b is configured so that a predetermined reagent can be mixed with the aspirated blood. That is, the sampling valve 21b is configured so that a diluted sample in which a predetermined amount of reagent supplied from the reagent preparing device 4 is mixed in a predetermined amount of blood can be generated.

The reaction chamber 21c is configured so that a predetermined staining fluid is further mixed to the diluted sample supplied from the sampling valve 21b and reacts with it for a predetermined time. The measurement sample preparing unit 21 thus has a function of preparing the white blood cell measurement sample in which the white blood cells are stained and the red blood cells are hemolyzed. The measurement sample preparing unit 21 also has a function of preparing the reticulocyte measurement sample in which the reticulocyte is stained and a function of preparing the blood platelet measurement sample in which the blood platelet is stained.

The measurement sample preparing unit 21 is also configured to supply the white blood cell measurement sample with the sheath liquid from the measurement sample preparing unit 21 to the sheath flow cell 22c described later (see FIG. 4) at the time of a white blood cell differential measurement (hereinafter also referred to as "DIFF measurement") mode. The measurement sample preparing unit 21 is also configured to supply the reticulocyte measurement sample with the sheath liquid from the measurement sample preparing unit 21 to the sheath flow cell 22c at the time of a reticulocyte measurement (hereinafter also referred to as "RET measurement") mode. Furthermore, the measurement sample preparing unit 21 is also configured to supply the blood platelet measurement sample with the sheath liquid from the measurement sample preparing unit 21 to the sheath flow cell 22c at the time of a blood platelet measurement (hereinafter also referred to as "PLT measurement") mode.

Figure 4:
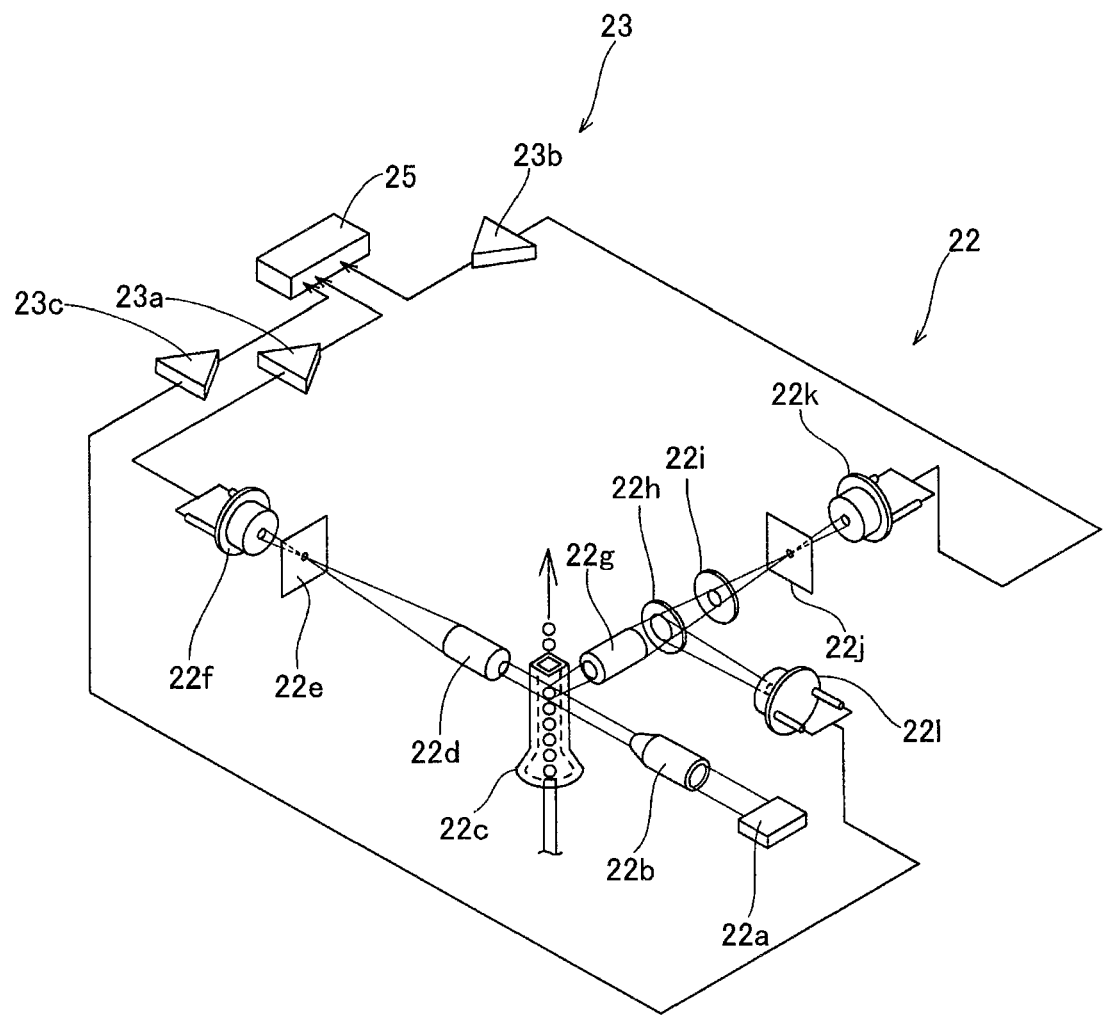
FIG. 4 is a schematic view showing a detection unit of the blood analyzer including the reagent preparing device according to the first embodiment shown in FIG. 1.

As shown in FIG. 4, the detection unit 22 includes a light emitting portion 22a for emitting laser light, an irradiation lens unit 22b, the sheath flow cell 22c irradiated with laser light, a light collecting lens 22d arranged on an extended line in a direction the laser light emitted from the light emitting potion 22a advances, a pin hole 22e and a PD (Photo Diode) 22f, a light collecting lens 22g arranged in a direction intersecting the direction the laser light emitted from the light emitting portion 22a advances, a dichroic mirror 22h, an optical filter 22i, a pin hole 22j and an APD (Avalanche Photo Diode) 22k, and a PD 221 arranged at the side of the dichroic mirror 22h.

The light emitting portion 22a is arranged to emit light to the sample flow including the measurement sample that passes the inside of the sheath flow cell 22c. The irradiation lens unit 22b is arranged to convert the light emitted from the light emitting portion 22a to parallel light. The PD 22f is arranged to receive the forward scattered light output from the sheath flow cell 22c. The information on the size of the particle (blood cell) in the measurement sample can be obtained from the forward scattered light output from the sheath flow cell 22c.

The dichroic mirror 22h is arranged to separate the lateral scattered light and the lateral fluorescence output from the sheath flow cell 22c. Specifically, the dichroic mirror 22h is arranged to have the lateral scattered light output from the sheath flow cell 22c enter to the PD 221, and to have the lateral fluorescence output from the sheath flow cell 22c enter to the APD 22k. The PD 221 is arranged to receive the lateral scattered light. Internal information, for example, the size of the core of the particle (blood cell) in the measurement sample can be obtained from the lateral scattered light output from the sheath flow cell 22c. The APD 22k is arranged to receive the lateral fluorescence. Information on the staining degree of the particle (blood cell) in the measurement sample can be obtained from the lateral fluorescence output from the sheath flow cell 22c. The PD 22f, 221, and the APD 22k respectively have a function of converting the received optical signal to an electrical signal.

As shown in FIG. 4, the analog processing unit 23 includes amplifiers 23a, 23b, and 23c. The amplifiers 23a, 23b, and 23c are respectively arranged to perform amplification and waveform processing on the electrical signal output from the PD 22f, 221, and the APD 22k.

As shown in FIG. 2, the microcomputer 25 includes a control portion 251 including a control processor and a memory for operating the control processor, an A/D converter 252 for converting a signal output from the analog processing unit 23 to a digital signal, and a calculating portion 253 for performing a predetermined process on the digital signal output from the A/D converter 252.

The control portion 251 has a function of controlling the measurement sample preparing unit 21 and the detection unit 22 through a bus 254a and an interface 255a. The control portion 251 is connected with the display/operation unit 24 through the bus 254a and an interface 255b, and connected with the data processing section 3 through a bus 254b and an interface 255c. The calculating portion 253 has a function of outputting a calculation result to the control portion 251 through an interface 255d and the bus 254a. The control portion 251 has a function of transmitting the calculation result (measurement data) to the data processing section 3.

Figure 5:
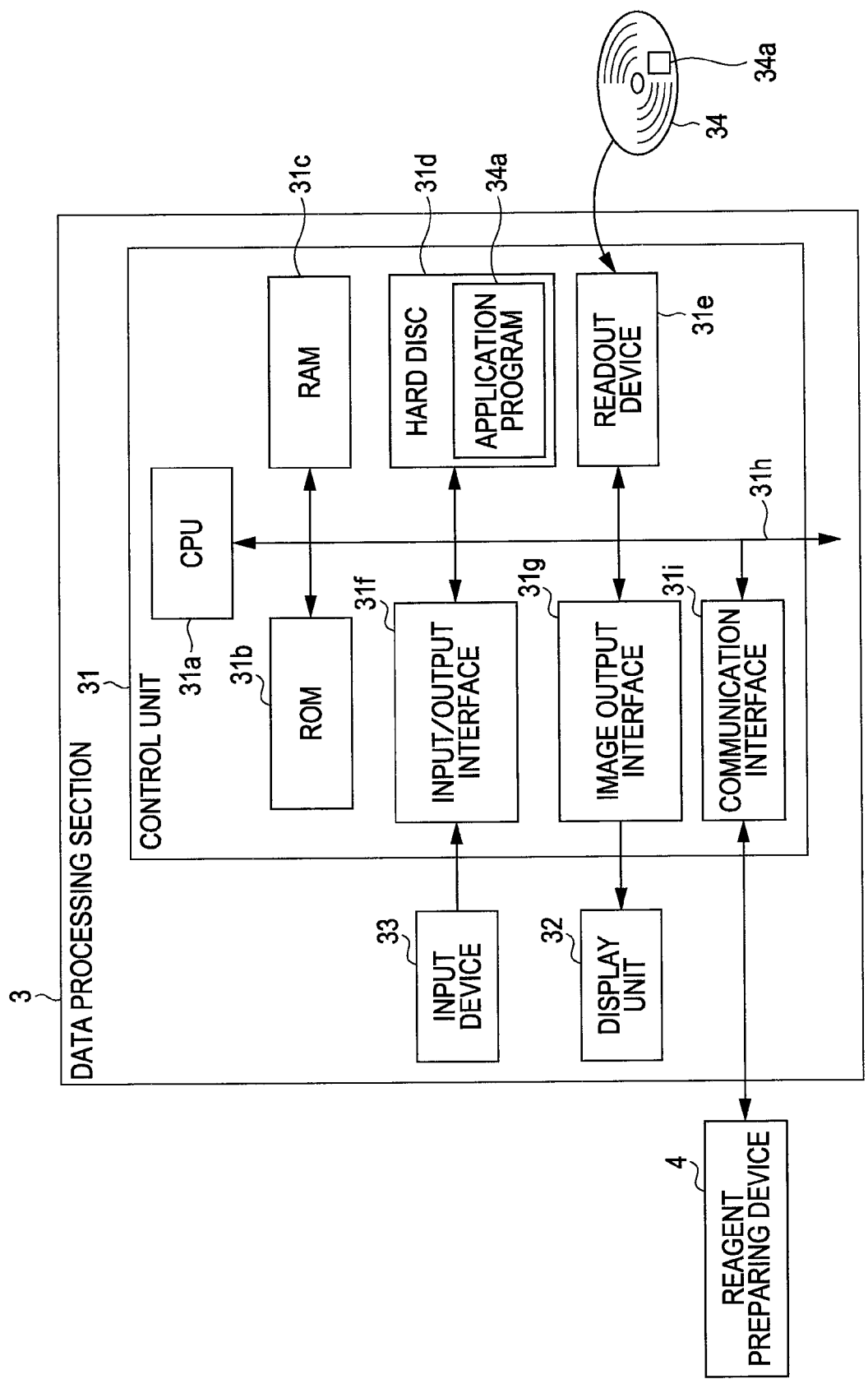
FIG. 5 is a block diagram showing a configuration of a data processing section of the blood analyzer including the reagent preparing device according to the first embodiment shown in FIG. 1.

As shown in FIG. 1, the data processing section 3 includes a personal computer (PC) and the like, and has a function of analyzing the measurement data of the measurement section 2 and displaying the analysis result. The data processing section 3 includes a control unit 31, a display unit 32, and an input device 33, as shown in FIG. 5.

The control unit 31 has a function of transmitting a measurement start signal including the measurement mode information and a shutdown signal to the measurement section 2. As shown in FIG. 5, the control unit 31 is also configured by a CPU 31a, a ROM 31b, a RAM 31c, a hard disc 31d, a readout device 31e, an input/output interface 31f, an image output interface 31g and a communication interface 31i. The CPU 31a, the ROM 31b, the RAM 31c, the hard disc 31d, the readout device 31e, the input/output interface 31f, the image output interface 31g and the communication interface 31i are connected by a bus 31h.

The CPU 31a is arranged to execute computer programs stored in the ROM 31b and the computer programs loaded in the RAM 31c. The ROM 31b is configured by mask ROM, PROM, EPROM, EEPROM, and the like, and is recorded with computer programs to be executed by the CPU 31a, data used for the same, and the like.

The RAM 31c is configured by SRAM, DRAM and the like. The RAM 31c is used to read out the computer programs recorded on the ROM 31b and the hard disc 31d. The RAM 31c is used as a work region of the CPU 31a when executing the computer programs.

The hard disc 31d is installed with various computer programs to be executed by the CPU 31a such as operating system and application program, as well as data used in executing the computer program. The application program 34a described later is also installed in the hard disc 31d.

The readout device 31e is configured by flexible disc drive, CD-ROM drive, DVD-ROM drive and the like, and is able to read out computer programs and data recorded on a portable recording medium 34. The application program 34a causing the computer to implement a predetermined function is stored in the portable recording medium 34. The computer serving as the data processing section 3 reads out the application program 34a from the portable recording medium 34, and installs the application program 34a to the hard disc 31d.

The application program 34a is not only provided by the portable recording medium 34, and may be provided through an electrical communication line (wired or wireless) from external devices communicably connected with the data processing section 3 by the electrical communication line. For instance, the application program 34a may be stored in the hard disc of the server computer on the Internet, wherein the data processing section 3 can access the server computer to download the application program 34a and install the application program 34a in the hard disc 31d.

Operating system providing graphical user interface environment such as Windows (registered trademark) manufactured and sold by US Microsoft Co. is installed in the hard disc 31d. In the following description, the application program 34a according to the first embodiment is assumed to be operating on the operating system.

The input/output interface 31f is configured by serial interface such as USB, IEEE1394 and RS-232C; parallel interface such as SCSI, IDE and IEEE1284; analog interface such as a D/A converter and an A/D converter, and the like. The input device 33 including a keyboard and a mouse is connected to the input/output interface 31f, so that the user can input data to the data processing section 3 using the input device 33. The user can also select the measurement mode, and activate and shut down the measurement section 2 and the reagent preparing device 4 using the input device 33. For instance, when the user instructs to activate or shut down using the input device 33, an activation signal or a shut down signal is transmitted to the reagent preparing device 4 through the communication interface 31i.

The image output interface 31g is connected to the display unit 32 configured by LCD, CRT or the like, and is configured to output a video signal corresponding to the image data provided from the CPU 31a to the display unit 32. The display unit 32 displays the image (screen) according to the input video signal.

In the first embodiment, the reagent preparing device 4 is arranged to prepare the reagent to be used in the measurement sample preparing unit 21 of the measurement section 2. Specifically, the reagent preparing device 4 is configured to prepare the reagent used in blood analysis by diluting a high concentration reagent to a desired concentration using the RO water produced from the tap water. The RO water is one type of pure water and is water in which impurities are removed by being transmitted through an RO (Reverse Osmosis) membrane (reverse osmosis membrane). Other than the RO water, the pure water includes purified water, deionized water and distilled water, and is water subjected to the process of removing impurities, and the purity is not particularly limited.

Figure 6:
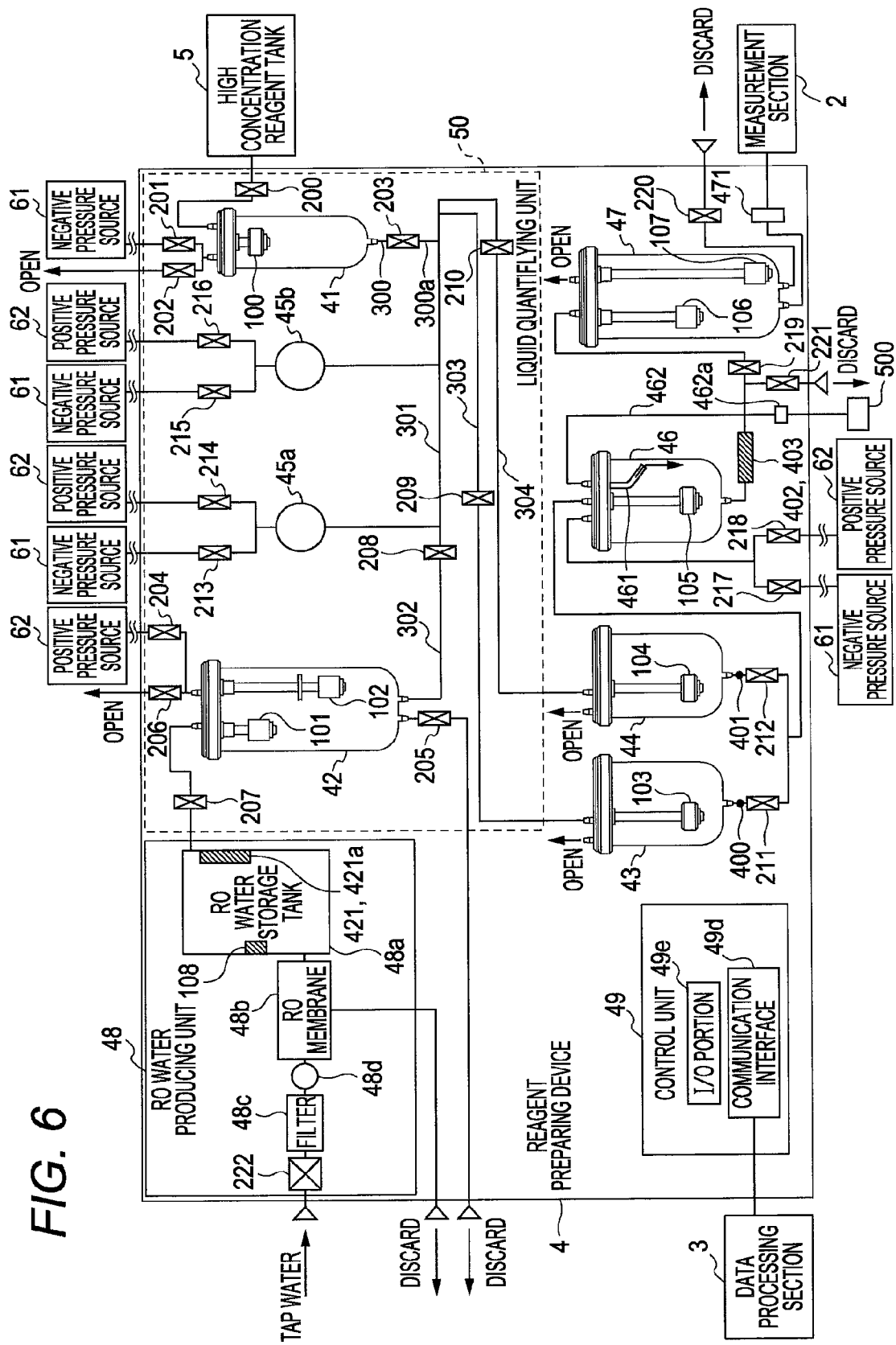
FIG. 6 is a block diagram showing a configuration of the reagent preparing device according to the first embodiment shown in FIG. 1.

As shown in FIG. 6, the reagent preparing device 4 includes a high concentration reagent chamber 41, an RO water chamber 42, two diluting chambers 43 and 44, two diaphragm pumps 45a and 45b, a stirring chamber 46, a supply chamber 47, an RO water producing unit 48, and a control unit 49 for controlling each unit of the reagent preparing device 4. The reagent preparing device 4 also includes a pneumatic unit 6 (see FIG. 1) installed at the exterior of the housing, and is configured to send each liquid in the device using negative pressure and positive pressure supplied from the pneumatic unit 6. The pneumatic unit 6 includes a negative pressure source 61 for supplying negative pressure and a positive pressure source 62 for supplying positive pressure to the reagent preparing device 4. The reagent preparing device 4 includes a display unit 4a (see FIG. 1) of touch panel type. The CPU 49a of the control unit 49 of the reagent preparing device 4 is configured to accept instructions such as activation, shut-down, and various settings of the reagent preparing device 4 from the use through the display unit 4a of touch panel type.

The high concentration reagent chamber 41 is configured to supply the high concentration reagent from a high concentration reagent tank 5. The high concentration reagent chamber 41 includes a float switch 100 for detecting that a predetermined amount of high concentration reagent is stored in the chamber. The float switch 100 is configured such that the float portion moves up and down according to the liquid amount (liquid level) in the high concentration reagent chamber 41. Each unit is controlled by the control unit 49 such that the high concentration reagent is supplied from the high concentration reagent tank 5 to the high concentration reagent chamber 41 when the float portion of the float switch 100 reaches the lower limit. Furthermore, each unit is controlled by the control unit 49 such that the supply of the high concentration reagent from the high concentration reagent tank 5 to the high concentration reagent chamber 41 is stopped when the float portion of the float switch 100 reaches the upper limit. The float switch 100 is arranged near the upper end of the high concentration reagent chamber 41, and is configured such that the float portion reaches the upper limit when about 300 mL of the high concentration reagent is stored in the high concentration reagent chamber 41. The high concentration reagent is thus supplied such that about 300 mL is stored in the high concentration reagent chamber 41 on a constant basis.

The high concentration reagent chamber 41 is connected to the high concentration reagent tank 5 through an electromagnetic valve 200, and is connected to the negative pressure source 61 of the pneumatic unit 6 through an electromagnetic valve 201. The high concentration reagent chamber 41 is also configured to be opened to atmosphere or closed by the opening and closing of the electromagnetic valve 202. The high concentration reagent chamber 41 is connected to a flow path 301 for transferring the liquid from the diaphragm pump 45a (45b) to the diluting chamber 43 (44) by the flow path 300. An electromagnetic valve 203 is arranged on the flow path 300, which electromagnetic valve 203 is arranged near the flow path 301.

The RO water chamber 42 is configured such that the RO water for diluting the high concentration reagent is supplied from the RO water producing unit 48.

The RO water chamber 42 includes float switches 101 and 102 for detecting that the RO water stored in the chamber has reached the upper limit amount and the lower limit amount, respectively. The float switch 101 (102) is configured such that the float portion moves up and down according to the liquid amount (liquid level) in the RO water reagent chamber 42. Each unit is controlled by the control unit 49 such that the supply of RO water from the RO water producing unit 48 to the RO water chamber 42 is stopped when the float portion of the float switch 101 reaches the position corresponding to the upper limit amount. Furthermore, each unit is controlled by the control unit 49 such that the RO water is supplied from the RO water producing unit 48 to the RO water chamber 42 when the float portion of the float switch 102 reaches the position corresponding to the lower limit amount. The float switch 101 is arranged near the upper end of the RO water chamber 42, and is configured such that the float portion reaches the position corresponding to the upper limit amount of the RO water chamber 42 when about 600 mL of the RO water is stored in the RO water chamber 42. The float switch 102 is configured such that the float portion reaches the position corresponding to the lower limit amount of the RO water chamber 42 when the RO water stored in the RO water chamber 42 reduces to about 300 mL. The RO water of greater than or equal to about 300 mL and less than or equal to about 600 mL is thus stored in the RO water chamber 42 while the reagent preparing device 4 is operating.

The RO water chamber 42 is configured so that the RO water in the chamber can be discarded. Specifically, the RO water chamber 42 is connected to the positive pressure source 62 through the electromagnetic valve 204 and connected to a discard flow path through the electromagnetic valve 205, so that the RO water inside is pushed out to the discard flow path by the positive pressure force by opening both electromagnetic valves 204 and 205. The RO water chamber 42 is configured to be opened to atmosphere and closed by the opening and closing of the electromagnetic valve 206. The RO water chamber 42 is connected to the RO water storage tank 48a, to be hereinafter described, of the RO water producing unit 48 through the electromagnetic valve 207. The RO water chamber 42 is connected to the diaphragm pumps 45a and 45b by the flow path 302 through the electromagnetic valve 208.

The diluting chambers 43 and 44 are respectively arranged to dilute the high concentration reagent with the RO water. As hereinafter described, the diluting chamber 43 (44) is configured to store about 300 mL of liquid (mixed solution of high concentration reagent and RO water) sent by the diaphragm pumps 45a and 45b. The diluting chamber 43 (44) includes a float switch 103 (104) for detecting that the remaining amount of the liquid (mixed solution of high concentration reagent and RO water) stored in the chamber has reached a predetermined amount. The float switch 103 (104) is configured such that the float portion moves up and down according to the liquid amount (liquid level) in the diluting chamber 43 (44). The diluting chamber 43 (44) is configured so as to be always opened to atmosphere. The diluting chamber 43 (44) is connected to the flow path 301 by the flow path 303 (304) through the electromagnetic valve 209 (210). The flow path 303 (304) has an inner diameter of about 4 mm, similar to the flow path 301. The liquid (RO water and high concentration reagent) transferred through the flow path 301 can be transferred to the diluting chamber 43 by opening the electromagnetic valve 209 with the electromagnetic valve 210 closed. The liquid (RO water and high concentration reagent) transferred through the flow path 301 can be transferred to the diluting chamber 43 by opening the electromagnetic valve 210 with the electromagnetic valve 209 closed. In other words, the electromagnetic valves 209 and 210 are respectively configured to function as a flow path switching unit of the flow paths 303 and 304.

The diluting chamber 43 (44) is connected to the stirring chamber 46 through the electromagnetic valve 211 (212). An air bubble sensor 400 (401) is arranged between the diluting chamber 43 (44) and the electromagnetic valve 211 (212). The air bubble sensor 400 (401) is a transmissive sensor, and is configured to detect air bubbles that pass the flow path. Whether or not the liquid (mixed solution of high concentration reagent and RO water) in the diluting chamber 43 (44) are all discharged can be checked by the control unit 49 when the float portion of the float switch 103 (104) reaches the lower limit and the air bubbles are detected by the air bubble sensor 400 (401). When the diluting chamber 43 (44) becomes empty (all liquid in the chamber is discharged), each unit is controlled by the control unit 49 so that the high concentration reagent and the RO water are supplied to the empty diluting chamber 43 (44).

The diaphragm pumps 45a and 45b have similar configuration with respect to each other, and are configured to perform the same operation at the same time. The diaphragm pump 45a (45b) has a function of quantifying about 6.0 mL (constant amount) of the high concentration reagent and the RO water in one quantifying operation. The diaphragm pump 45a (45b) is connected to the negative pressure source 61 through the electromagnetic valve 213 (215), and also connected to the positive pressure source 62 through the electromagnetic valve 214 (216). The high concentration reagent chamber 41, the RO water chamber 42, the diaphragm pumps 45a and 45b, the pneumatic unit 6, the flow paths 300 to 304, and the electromagnetic valves 200 to 210 and 213 to 216 configure the liquid quantifying unit 50 (see FIG. 6) of the reagent preparing device 4.

As shown in FIG. 6, the stirring chamber 46 is configured to accommodate about 300 mL of liquid, and is arranged to stir the liquid (mixed solution of high concentration reagent and RO water) transferred from the diluting chamber 43 (44). Specifically, the stirring chamber 46 includes a bent pipe 461, and is configured so that the liquid (mixed solution of high concentration reagent and RO water) transferred from the diluting chamber 43 (44) flows into the stirring chamber 46 along the inner wall surface of the stirring chamber 46 by passing the pipe 461. The liquid (mixed solution of high concentration reagent and RO water) transferred from the diluting chamber 43 (44) thus flows along the inner wall surface of the stirring chamber 46, whereby convection occurs and the high concentration reagent and the RO water are easily stirred. The high concentration reagent and the RO water are stirred to a certain extent in the diluting chamber 43 (44) and in the flow path from the diluting chamber 43 (44) to the stirring chamber 46, but the solution is more reliably stirred by configuring the stirring chamber 46 in the above manner.

As shown in FIG. 6, in the first embodiment, the stirring chamber 46 includes an introducing path 462 for introducing a standard liquid (standard reagent) from the standard liquid accommodation container 500 used when calibrating the electrical conductivity meter, to be hereinafter described. A plug 462a is arranged at the distal end of the introducing path 462. When introducing the standard liquid, the user removes the plug 462a at the distal end of the introducing path 462, and connects the standard liquid accommodation container 500 to the introducing path 462. The standard liquid (standard reagent) of the standard liquid accommodation container 500 is a liquid containing the component same as the component contained in the reagent prepared by the reagent preparing device 4 at the same concentration.

The stirring chamber 46 includes a float switch 105 for detecting that the remaining amount of the liquid (mixed solution of high concentration reagent and RO water) accommodated in the chamber has reached a predetermined amount. The float switch 105 is configured such that the float portion moves up and down according to the liquid amount (liquid level) in the stirring chamber 46. Each unit is controlled by the control unit 49 such that about 300 mL of mixed solution is supplied from either diluting chamber 43 or 44 to the stirring chamber 46 when the float portion of the float switch 105 reaches the lower limit and the interior of the chamber becomes empty. When the mixed solution supplied from either diluting chamber 43 or 44 and stirred is discharged from the stirring chamber 46, about 300 mL of mixed solution is then supplied from the other diluting chamber 43 or 44 to the stirring chamber 46. The stirring chamber 46 is connected to the negative pressure source 61 through the electromagnetic valve 217, and connected to the positive pressure source 62 through the electromagnetic valve 218.

The supply chamber 47 is arranged to store a predetermined amount of reagent to supply to the measurement section 2. The supply chamber 47 includes a float switch 106 for detecting that the remaining amount of reagent stored in the chamber has reached about 300 mL. The supply chamber 47 also includes a float switch 107 for detecting that the remaining amount of reagent stored in the supply chamber 47 is substantially zero. The float switch 106 (107) is configured such that the float portion moves up and down according to the liquid amount (liquid level) in the supply chamber 47. The float portion of the float switch 106 is configured to be movable from the vicinity of the upper end in the height direction of the supply chamber 47 to the intermediate position. Each unit is controlled by the control unit 49 so that about 300 mL of reagent of the desired concentration is supplied from the stirring chamber 46 to the supply chamber 47 when the float portion of the float switch 106 reaches the intermediate position in the height direction of the supply chamber 47 (lower limit position in the movable range of the float portion of the float switch 106). The reagent of desired concentration of greater than or equal to about 300 mL and less than or equal to about 600 mL is stored in the supply chamber 47 on a constant basis. The reagent can be rapidly supplied to the measurement section 2 according to the supply instruction by storing a predetermined amount of reagent in the supply chamber 47.

The float portion of the float switch 107 is configured to be movable to the vicinity of the bottom of the supply chamber 47. The supply of reagent to the measurement section 2 is stopped when detected that the remaining amount of reagent accommodated in the chamber is substantially zero by the float switch 107. Therefore, the air bubbles are prevented from mixing to the reagent to be supplied to the measurement section 2 while continuing the supply of reagent to the measurement section 2 as much as possible even if the reagent is not transferred to the supply chamber 47 for some reasons.

The supply chamber 47 is connected to the stirring chamber 46 through the electromagnetic valve 219. The supply chamber 47 is configured so that the reagent in the chamber can be discarded at the time of maintenance and the like by opening the electromagnetic valve 220. The supply chamber 47 is configured so as to be opened to atmosphere on a constant basis. The supply chamber 47 is connected to the measurement section 2 through the filter 471. The filter 471 is arranged to prevent impurities from mixing in the reagent to be supplied to the measurement section 2.

As shown in FIG. 6, in the first embodiment, an electrical conductivity acquiring unit 402 for measuring the electrical conductivity of the reagent is arranged between the stirring chamber 46 and the supply chamber 47. Since the concentration and the electrical conductivity of the reagent have a predetermined relationship, the concentration of the reagent can be determined by measuring the electrical conductivity of the reagent. A discarding flow path is connected between the electrical conductivity acquiring unit 402 and the electromagnetic valve 219 by way of the electromagnetic valve 221. If the concentration of the reagent is not the desired concentration based on the electrical conductivity, the relevant reagent is discarded through the discarding flow path. The detailed structure of the electrical conductivity acquiring unit 402 will be described below with reference to FIGS. 7 and 8.

Figure 7:
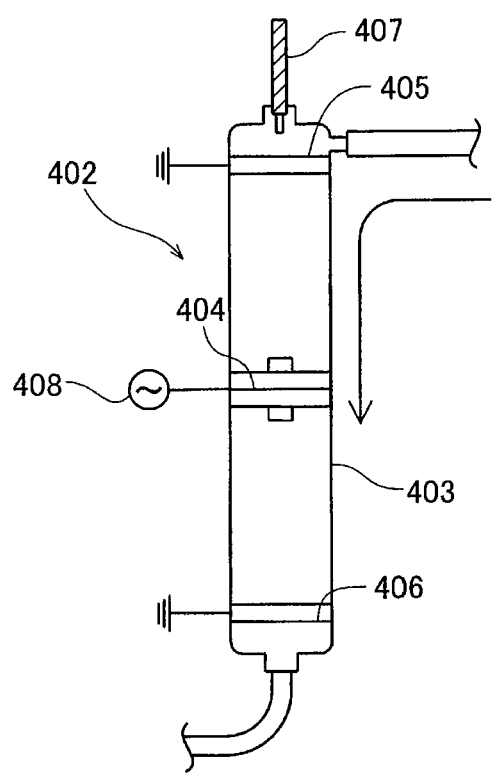
FIG. 7 is a schematic view showing an electrical conductivity acquiring unit of the reagent preparing device according to the first embodiment shown in FIG. 6.
Figure 8:
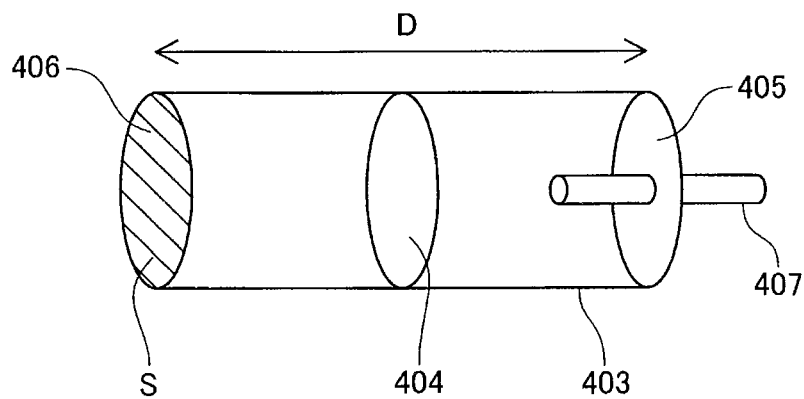
FIG. 8 is a schematic view showing the electrical conductivity acquiring unit of the reagent preparing device according to the first embodiment shown in FIG. 6.

As shown in FIGS. 7 and 8, the electrical conductivity acquiring unit 402 includes a tubular body 403 connected to the stirring chamber 46 and the supply chamber 47, where three electrodes 404, 405, and 406, and a thermistor 407 for measuring the temperature of the reagent are arranged in the tubular body 403. The electrode 404 is connected to an AC power supply 408, and the electrodes 405 and 406 are grounded. The electrode 405 and the electrode 406 are arranged with a predetermined distance D. In the first embodiment, the current flows between the electrodes 404 and 405, and between the electrodes 404 and 406 through the reagent when voltage is applied by the AC power supply 408, and the resistance of the reagent between the electrodes 404 and 405, and between the electrodes 404 and 406 is measured. The thermistor 407 is arranged to project out to the interior of the tubular body 403, and is configured to contact the reagent flowing through the tubular body 403. When the thermistor 407 contacts the reagent, the temperature of the thermistor 407 and the reagent become substantially the same, and thus the resistance value of the thermistor 407 becomes a resistance value reflecting the temperature of the reagent.

Figure 9:
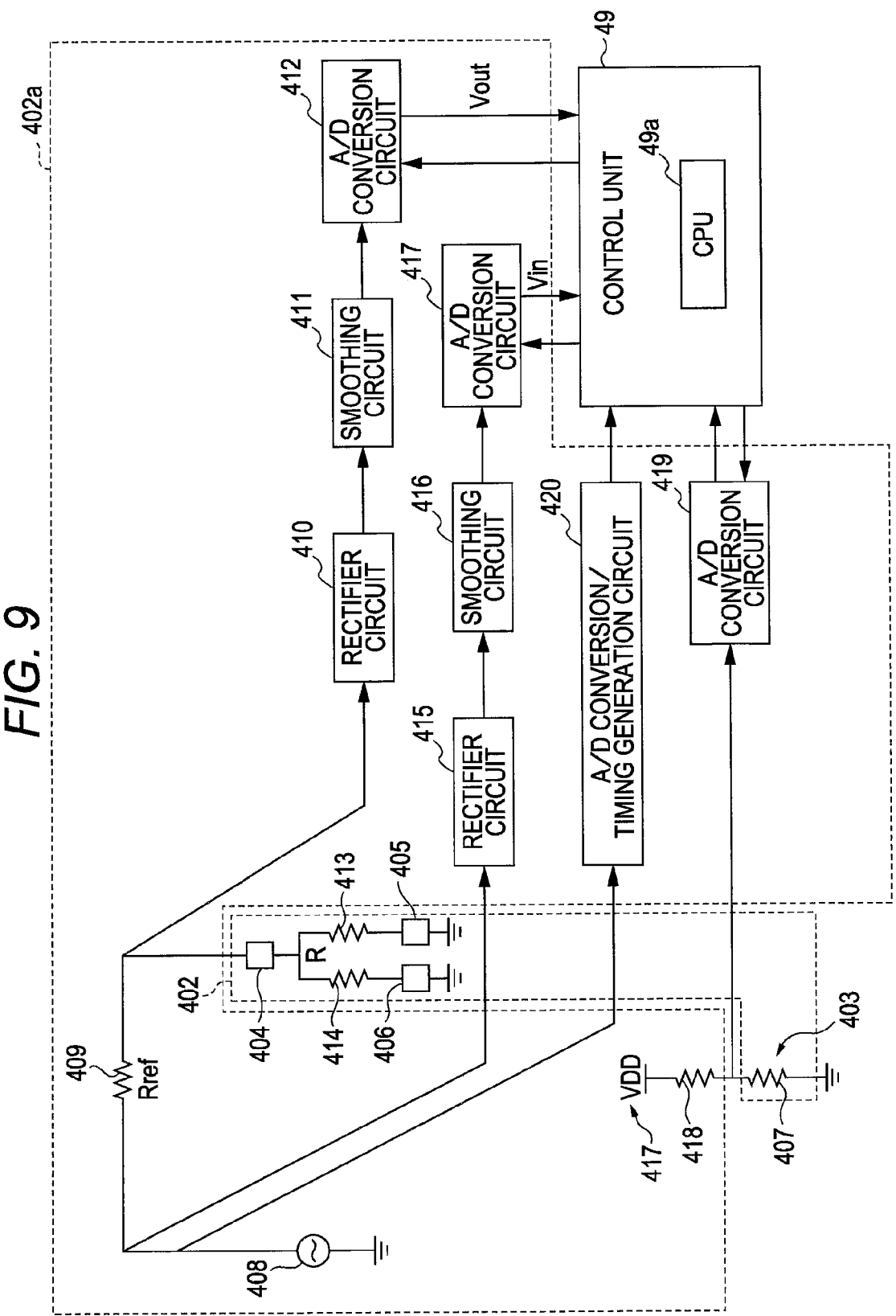
FIG. 9 is an equivalent circuit diagram showing a circuit for performing the measurement of the electrical conductivity and the temperature by the electrical conductivity acquiring unit shown in FIG. 7.
Figure 10:
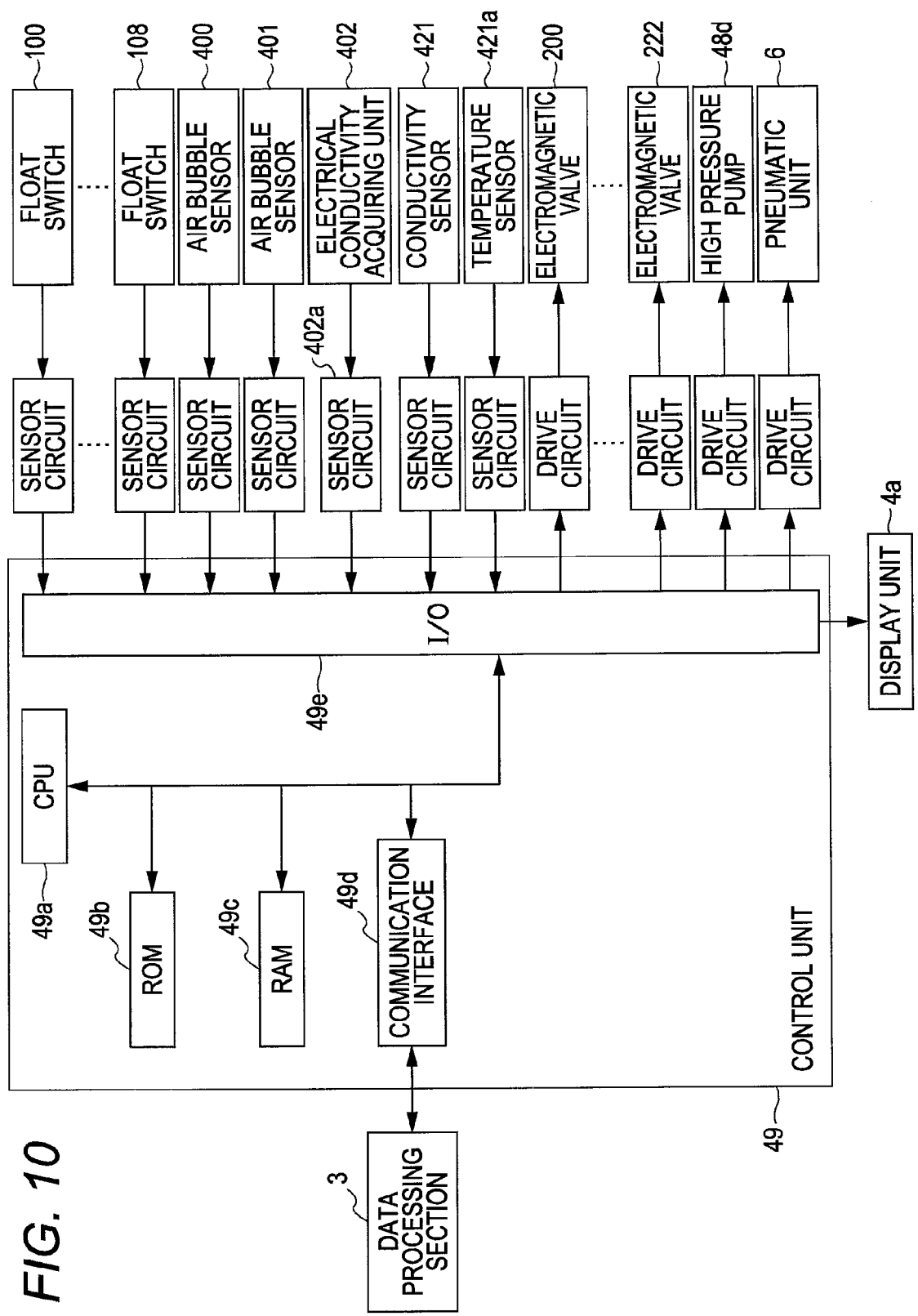
FIG. 10 is a block diagram explaining a control unit of the reagent preparing device according to the first embodiment of the present invention.

As shown in FIGS. 9 and 10, the electrical conductivity acquiring unit 402 is electrically connected with the control unit 49 through the sensor circuit 402a. The electrical conductivity acquiring unit 402, the sensor circuit 402a, and the control unit 49 configure an electrical conductivity meter for measuring the electrical conductivity of the reagent and a thermometer for measuring the temperature of the reagent.

As shown in an equivalent circuit diagram of FIG. 9, the AC power supply 408 is connected to a reference resistor 409 having a known value. The reference resistor 409 is connected to the electrode 404. The reference resistor 409 and the electrode 404 are connected to the control unit 49 through a rectifier circuit 410, a smoothing circuit 411 and an A/D conversion circuit 412. The electrode 404 is connected to the electrode 405 through the resistor (resistor 413) of the reagent between the electrodes 404 and 405, and is also connected to the electrode 406 through the resistor (resistor 414) of the reagent between the electrodes 404 and 406. The voltage output from the smoothing circuit 411 after input from the electrode 404 to the smoothing circuit 411 through the rectifier circuit 410 is a voltage reflecting the voltage to be applied to the resistor of the reagent. The voltage is A/D converted by the A/D conversion circuit 412, and then input to the control unit 49 as a measurement voltage Vout.

The AC power supply 408 is connected to the control unit 49 through the rectifier circuit 415, the smoothing circuit 416, and the A/D conversion circuit 417. The output voltage of the smoothing circuit 416 is a voltage that becomes a reference when calculating the electrical conductivity of the reagent, and such voltage is also A/D converted by the A/D conversion circuit 417 and input to the control unit 49 as a reference voltage Vin. The electrical conductivity of the reagent can be acquired by the control unit based on the ratio of the measurement voltage Vout with respect to the reference voltage Vin.

The thermistor 407 of the electrical conductivity acquiring unit 402 is connected to the DC power supply Vdd 417 through the resistor 418 having a known resistance value. The resistor 418 and the thermistor 407 are connected to the control unit 49 through the A/D conversion circuit 419. The temperature of the thermistor 407 (temperature of the reagent) can be measured based on the output voltage of the A/D conversion circuit 419.

The AC power supply 408 is directly connected to an A/D conversion/timing generation circuit 420. The timing of conversion of the A/D conversion circuits 412, 417, and 419 is determined based on the timing of conversion from the analog data to the digital data by the A/D conversion/timing generation circuit 420 directly connected to the AC power supply 408. The A/D converted data is input to the CPU 49a in the control unit 49. The CPU 49a calculates the electrical conductivity of the reagent based on the input data from the A/D conversion circuits 412 and 417, and calculates the temperature of the reagent based on the data from the A/D conversion circuit 419. The calculation of the electrical conductivity and the temperature of the reagent will be specifically described later.

As shown in FIG. 6, the RO water producing unit 48 is configured to produce the RO water serving as a diluting liquid for diluting the high concentration reagent using tap water. The RO water producing unit 48 includes an RO water storage tank 48a, an RO membrane 48b, and a filter 48c for protecting the RO membrane 48b by removing impurities contained in the tap water. Furthermore, the RO water producing unit 48 includes a high pressure pump 48d for applying high pressure to the water passed through the filter 48c so that water molecules transmit through the RO membrane 48b, and an electromagnetic valve 222 for controlling the supply of tap water.

The RO water storage tank 48a is arranged to store the RO water transmitted through the RO film 48b. The RO water storage tank 48a includes a float switch 108 for detecting that a predetermined amount of RO water is stored. The RO water storage tank 48a includes a conductivity sensor 421 for measuring the electrical conductivity of the RO water in the RO water storage tank 48a. The conductivity sensor 421 includes a temperature sensor 421a for measuring the temperature of the RO water. The speed at which the RO water is supplied from the RO water producing unit 48 to the RO water storage tank 48a, that is, the production speed of the RO water by the RO water producing unit 48 is greater than or equal to about 20 L/hour and smaller than or equal to about 50 L/hour.

As shown in FIG. 10, the control unit 49 includes a CPU 49a, a ROM 49b, a RAM 49c, a communication interface 49d connected to the data processing section 3, and an I/O (Input/Output) portion 49e connected to each unit in the reagent preparing device 4 through each circuit.

The CPU 49a can execute computer programs stored in the ROM 49b and the computer programs loaded in the RAM 49c. The CPU 49a is configured to use the RAM 49c as a work region when executing the computer programs. The control unit 49 includes a memory (49b) for storing various types of setting information. The memory 49b stores a value (known value) of the electrical conductivity of a standard liquid at a predetermined temperature, a correction value (P or P1) for correcting the electrical conductivity of the reagent calculated based on the measurement data, to be described later, and the like. The value of the electrical conductivity of the standard liquid at the predetermined temperature may be stored in the memory 49b in advance or may be input by the user. The input may be accepted by the input unit 33 of the data processing section 3, or an input device may be arranged in the reagent preparing device 4 and the input may be accepted by the input device.

A general formula for obtaining a target value of the electrical conductivity of the reagent is expressed with the following equation (1).

$$Z_0 = \{X + (A+1)Y\}/A \tag{1}$$

In the equation (1), $Z_0$ is, at 25° C., the target value (ms/cm) of the electrical conductivity of the reagent in which the high concentration reagent and the RO water are mixed and stirred, X is the electrical conductivity (ms/cm) of the high concentration reagent at 25° C., Y is the electrical conductivity (ms/cm) of the RO water at 25° C., and A is the diluting magnification (known) (25 times in the first embodiment). Here, X is a value unique to the high concentration reagent, and is a known value obtained through experiments and the like in advance.

The correction formula for taking into consideration the temperature of the RO water obtained by the temperature sensor 421a and the temperature of the reagent obtained by the thermistor 407 is expressed with the following equation (2).

$$Z = [\{X + (A-1)Y\}/A] \times \{1 + \alpha1(T2-25)\} = [[X+(A-1)Y1/\{1+\alpha0(T1-25)\}]/A] \times \{1+\alpha1(T2-25)\} \tag{2}$$

In the equation (2), Z is, at T2(° C.), the target value (ms/cm) of the electrical conductivity of the reagent in which the high concentration reagent and the RO water are mixed and stirred, Y1 is the electrical conductivity of the RO water at T1(° C.), T1 is the temperature of the RO water (° C.), T2 is the temperature (° C.) of the reagent in which the high concentration reagent and the RO water are mixed and stirred, $\alpha0$ is the temperature coefficient compared with the electrical conductivity of the RO water at 25(° C.), and $\alpha1$ is the temperature coefficient compared with the electrical conductivity of the reagent in which the high concentration reagent and the RO water are mixed and stirred, at 25(° C.). The temperature coefficients $\alpha0$ and $\alpha1$ differ depending on the type and concentration of the liquid, but are 0.02 for simplification in JIS (Japanese Industrial Standards).

In the first embodiment, the CPU 49a is configured to calculate the target value Z from the equation (2). Therefore, the CPU 49a determines the target value based on the desired diluting magnification A (known), the detection value Y1 of the electrical conductivity of the RO water, the measurement value T1 of the temperature of the RO water, the measurement value T2 of the temperature of the mixed and stirred reagent, and the electrical conductivity X (known) of the high concentration reagent. In the reagent preparing device 4, the reagent is prepared to become the target value. The CPU 49a compares the actual electrical conductivity of the prepared reagent and the target value to determine whether or not the prepared reagent has a desired concentration.

The calculation principle of the electrical conductivity of the prepared reagent performed by the CPU 49a will now be described with reference to FIGS. 8 and 9.

Assuming the resistance value of the known reference resistor 409 is Rref, the resistance value of the reagent (synthesized resistance of resistors 413 and 414) is R, the reference voltage is Vin, and the measurement voltage is Vout, the following equations (3) and (4) are satisfied in the equivalent circuit of FIG. 9.

$$V\text{out} = (V\text{in} \times R)/(R\text{ref} + R) \tag{3}$$

$$1/R = (V\text{in} - V\text{out})/(R\text{ref} \times V\text{out}) \tag{4}$$

Furthermore, assuming the electrical conductivity of the reagent when the temperature of the reagent is $\theta(° C.)$ is $\kappa(\theta)$, the electrical conductivity $\kappa(\theta)$ is defined as the following equation (5) using the inter-electrode distance D and the electrode area S of FIG. 8, $$\kappa(\theta) = (1/R) \times (D/S) \tag{5}$$

The value of (inter-electrode distance D/electrode area S) in equation (5) is a unique coefficient of the electrical conductivity acquiring unit 402.

Therefore, the electrical conductivity $\kappa(\theta)$ is defined as the following equation (6) from equations (4) and (5).

$$\kappa(\theta) = (V\text{in} - V\text{out})/(R\text{ref} \times V\text{out}) \times (D/S) \tag{6}$$

The values of the reference voltage Vin and the measurement voltage Vout are acquired by measurement, and the value of Rref is known, and thus the electrical conductivity $\kappa(\theta)$ of the reagent when the temperature of the reagent is $\theta(° C.)$ can be obtained if the value of the (inter-electrode distance D/electrode area S) can be obtained. The value of the (inter-electrode distance D/electrode area S) can be obtained through reverse calculation using equation (6) by performing a measurement in advance using a standard liquid with known electrical conductivity $\kappa(\theta)$.

In the first embodiment, the electrical conductivity $\kappa(\theta)$ when the temperature of the reagent is $\theta(° C.)$ can be corrected to the electrical conductivity $\kappa(25)$ when the temperature of the reagent is 25° C. based on the temperature $\theta$ of the reagent obtained by CPU 49a.

Specifically, assuming the temperature correction coefficient with respect to 25(° C.) of the electrical conductivity of the reagent as $f(\theta, 25)$, the following equation (7) can be satisfied.

$$\kappa(25) = \kappa(\theta) \times f(\theta, 25) \tag{7}$$

The temperature correction coefficient $f(\theta, 25)$ is expressed as the following equation (8) assuming the temperature change rate of the electrical conductivity of the reagent is 0.02 (2%).

$$f(\theta,25)=1+0.02\times(\theta-25) \qquad (8)$$

The electrical conductivity $\kappa(25)$ when the temperature of the reagent is 25° C. can be obtained based on the equations (7) and (8).

The calculation principle of the temperature $\theta$ of the reagent will now be described.

The resistance r of the thermistor 407 changes as in equation (9) using constants A and B with change in temperature.

$$r=A\exp(-B\theta) \qquad (9)$$

Assuming the voltage value of the DC power supply Vdd 417 is V0, the resistance value of the known resistor 418 is r0, the resolution of the A/D conversion circuit 419 is X, the maximum output voltage of the A/D conversion circuit 419 is V1, and the output value of the A/D conversion circuit 419 is Y, the following equation (10) can be satisfied.

$$Y\times V1/X=(r0\times V0)/(r0+r) \qquad (10)$$

Therefore, the temperature $\theta$ is expressed as the following equation (11) by equations (9) and (10).

$$\theta=-1/B\times Ln[r0/A/\{(V0\times X)/(V1\times Y)-1\}] \qquad (11)$$

In the first embodiment, the electrical conductivity meter including the electrical conductivity acquiring unit 402 and the control unit 49 can be calibrated. In other words, since the output value of the A/D conversion circuit 412 changes by degradation, corrosion, and the like of the electrodes 404 to 406 over the years, the electrical conductivity $\kappa(\theta)$ sometimes indicate a value different from the true electrical conductivity of the reagent. Thus, in the control unit 49, the electrical conductivity calculated by the CPU 49a using the data from the electrical conductivity acquiring unit 402 is corrected to indicate a true value by multiplying a predetermined correction value to the calculated electrical conductivity $\kappa(\theta)$. Therefore, the value $\kappa1(\theta)$ ultimately calculated by the CPU 49a as the electrical conductivity is expressed as the following equation (12) if the correction value is P.

$$\kappa1(\theta)=\kappa(\theta)\times P \qquad (12)$$

The calibration is performed by periodically changing the value of the correction value P so that the value of $\kappa1(\theta)$ becomes the true electrical conductivity. This value P has a default value of 1(100%). In other words, the value of $\kappa(\theta)$ is used as is for the final electrical conductivity at default.

Specifically, the correction value P is changed such that the calculated electrical conductivity $\kappa(\theta)$ becomes a true value by performing the calculation of the electrical conductivity $\kappa(\theta)$ by the electrical conductivity meter on the liquid (standard liquid) having a known electrical conductivity (true value is known). In other words, when the electrical conductivity $\kappa(\theta)$ is calculated for the standard liquid, the electrical conductivity of the standard liquid is known (e.g., 13.25 (mS/cm) when the temperature of the reagent is 25 degrees), and thus P1 is determined to satisfy $\kappa(25)\times P1=13.25$ when the correction value after the calibration is P1. Therefore, the following equation (13) is met. The electrical conductivity of the standard liquid, which is a known value, is stored in advance in the memory 49b of the control unit 49.

$$P1=13.25/\kappa(25) \qquad (13)$$

Furthermore, in the first embodiment, when the correction value P1 after the calibration is within a predetermined range (in the first embodiment 0.8(80%)≤P1≤1.2(120%)), the correction value P1 is made effective assuming the calibration is normally performed. The value of the electrical conductivity $\kappa1(\kappa)$ is acquired by the following equation (14) when the correction value P1 is made effective.

$$\kappa1(\kappa)=\kappa(\theta)\times P1 \qquad (14)$$

When the correction value P1 after the calibration is outside a predetermined range (in the first embodiment P1<0.8 (80%), P1>1.2(120%)), the change to the correction value P1 is not performed assuming the calibration is abnormal, and user is notified that calibration failed (change of correction value is not performed). Specifically, such notification is displayed on the display unit 4a of the reagent preparing device 4. The calibration process will be described in detail later.

The communication interface 49d is configured to transmit error information to the data processing section 3 so that the user can check the error that occurred in the reagent preparing device 4. The error information includes information for urging replacement of the high concentration reagent tank 5, information notifying that the RO water is no longer supplied, and information notifying the abnormality of the negative pressure source 61 and the positive pressure source 62. An error notification is displayed on the display unit 32 of the data processing section 3 based on the error information.

As shown in FIG. 10, the I/O portion 49e is configured to receive signals from the float switches 100 to 108, the air bubble sensors 400, 401, the electrical conductivity acquiring unit 402, the conductivity sensor 421 and the temperature sensor 421a through each sensor circuit. The I/O portion 49e is configured to output signals to each drive circuit to control the drive of the electromagnetic valves 200 to 222, the high pressure pump 48d, and the pneumatic unit 6 through each drive circuit.

The reagent preparation processing operation of the reagent preparing device 4 according to the first embodiment of the present invention will now be described with reference to FIGS. 6, 11, and 12.

The reagent preparation processing operation starts when the user instructs the activation of the device from the data processing section 3, that is, when the reagent preparing device 4 receives the activation signal from the data processing section 3. When the reagent preparation processing operation starts, initialization of the computer program stored in the ROM 49b is performed by the CPU 49a in step S11 of FIG. 11. In step S12, the CPU 49a determines whether or not the reagent preparing device 4 is normally shut down at the end of the previous operation. Specifically, determination is made based on a flag set to ON when normally shut down, as hereinafter described. The process proceeds to step S16 if normally shut down, and the process proceeds to step S13 if not normally shut down.

In step S13, the liquid in the chambers 42, 43, 44 and 46 other than the high concentration reagent chamber 41 and the supply chamber 47 are all discarded. Specifically, the electromagnetic valves 204 and 205 are opened with the electromagnetic valves 206, 207, and 208 closed by the CPU 49a to discard the RO water in the RO water chamber 42. The RO water discarded from the RO water chamber 42 may again be transferred to the RO water producing unit 48, and new RO water may be produced from the discarded RO water. Furthermore, the electromagnetic valves 218 and 221 are opened with the electromagnetic valves 211, 212, 217, and 219 closed by the CPU 49a to push out the mixed solution in the stirring chamber 46 to the discard flow path by the positive pressure force. The electromagnetic vales 211 and 217 are then opened with the electromagnetic valves 212, 218, 219, and 221 closed by the CPU 49a to transfer the mixed solution in the diluting chamber 43 to the stirring chamber 46 with the negative pressure force, and thereafter, the mixed solution is discarded from the stirring chamber 46 by the above-described operation. The mixed solution in the diluting chamber 44 also can be transferred to the stirring chamber 46 with the negative pressure force by opening the electromagnetic valves 212 and 217 with the electromagnetic valves 211, 218, 219, and 221 closed by the CPU 49a.

Therefore, the RO water having a possibility of being accumulated for a long time is prevented from being used in the reagent preparation, and the reagent of unknown diluting magnification is prevented from being prepared by discarding all liquids in the chambers 42, 43, 44, and 46 other than the high concentration reagent chamber 41 and the supply chamber 47 in step S13.

Thereafter, in step S14, the flow path, the RO water chamber 42, the diluting chamber 43 (44) and the stirring chamber 46 are cleaned. Specifically, about 12.0 mL (about 6.0 mL to each diaphragm pump) of RO water flows into the diaphragm pump 45a (45b) with the negative pressure force by opening the electromagnetic valves 206, 208, and 213 (215) by the CPU 49a after the RO water newly produced in the RO water producing unit 48 is supplied to the RO water chamber 42. The electromagnetic valves 214 (216) and 209 are then opened with the electromagnetic valves 208 and 213 (215) closed, so that about 12.0 mL (about 6.0 mL to each diaphragm pump) of RO water in the diaphragm pump 45a (45b) is transferred to the diluting chamber 43 with the positive pressure force. The above operations are repeated 25 times to supply about 300 mL of newly produced RO water to the diluting chamber 43.

About 300 mL of RO water is then transferred from the diluting chamber 43 to the stirring chamber 46 by opening the electromagnetic valves 211 and 217 by the CPU 49a. The RO water in the stirring chamber 46 is discarded by opening the electromagnetic valves 218 and 221 with the electromagnetic valves 217 and 219 closed by the CPU 49a.

While the RO water is being transferred from the diluting chamber 43 to the stirring chamber 46, about 300 mL of newly produced RO water is supplied to the diluting chamber 44 through the operation similar to the operation of transferring to the diluting chamber 43. The transfer of the RO water from the diluting chamber 44 to the stirring chamber 46 is also performed through the operation similar to the operation of transferring from the diluting chamber 43 to the stirring chamber 46. Therefore, the interior of the flow path, the RO water chamber 42, the diluting chamber 43 (44), and the stirring chamber 46 are cleaned with the newly produced RO water through the series of operations described above. A predetermined amount of RO water is already stored in the RO water chamber 42 through the operation similar to the RO water producing process of step S16, to be described later, before step S13.

In step S15, the reagent is prepared in the stirring chamber 46 through the operation similar to the operation of preparing the reagent of desired concentration, and all prepared reagent are discarded. Specifically, after the reagent of the desired concentration is supplied to the stirring chamber 46 by the operations of steps S21 and S22, described later, the reagent in the stirring chamber 46 is discarded by opening the electromagnetic valves 218 and 221 with the electromagnetic valves 217 and 219 closed by the CPU 49a. Thus, even if the reagent having a concentration exceeding the desired concentration remains in the flow path, the diluting chamber 43 (44) and the stirring chamber 46, the reagent can be suppressed from being prepared to the concentration other than the desired concentration since cleaning is carried out with the reagent of the desired concentration in addition to the cleaning by the RO water.

In step S16, the RO water producing process is performed in the RO water producing unit 48. In other words, the electromagnetic valve 222 shown in FIG. 6 is opened by the CPU 49a, so that the tap water passes through the filter 48c. The high pressure pump 48d is driven by the CPU 49a, and the water that passed the filter 48c transmits through the RO film 48b by high pressure. Whether or not a predetermined amount of RO water is accommodated in the RO water storage tank 48a is determined based on the detection result of the float switch 108. If the RO water does not meet a predetermined amount, the RO water is continuously supplied to the RO water storage tank 48a. If the RO water reached a predetermined amount, the electromagnetic valve 222 is closed, the drive of the high pressure pump 48d is stopped, and the operation is terminated.

Figure 11:
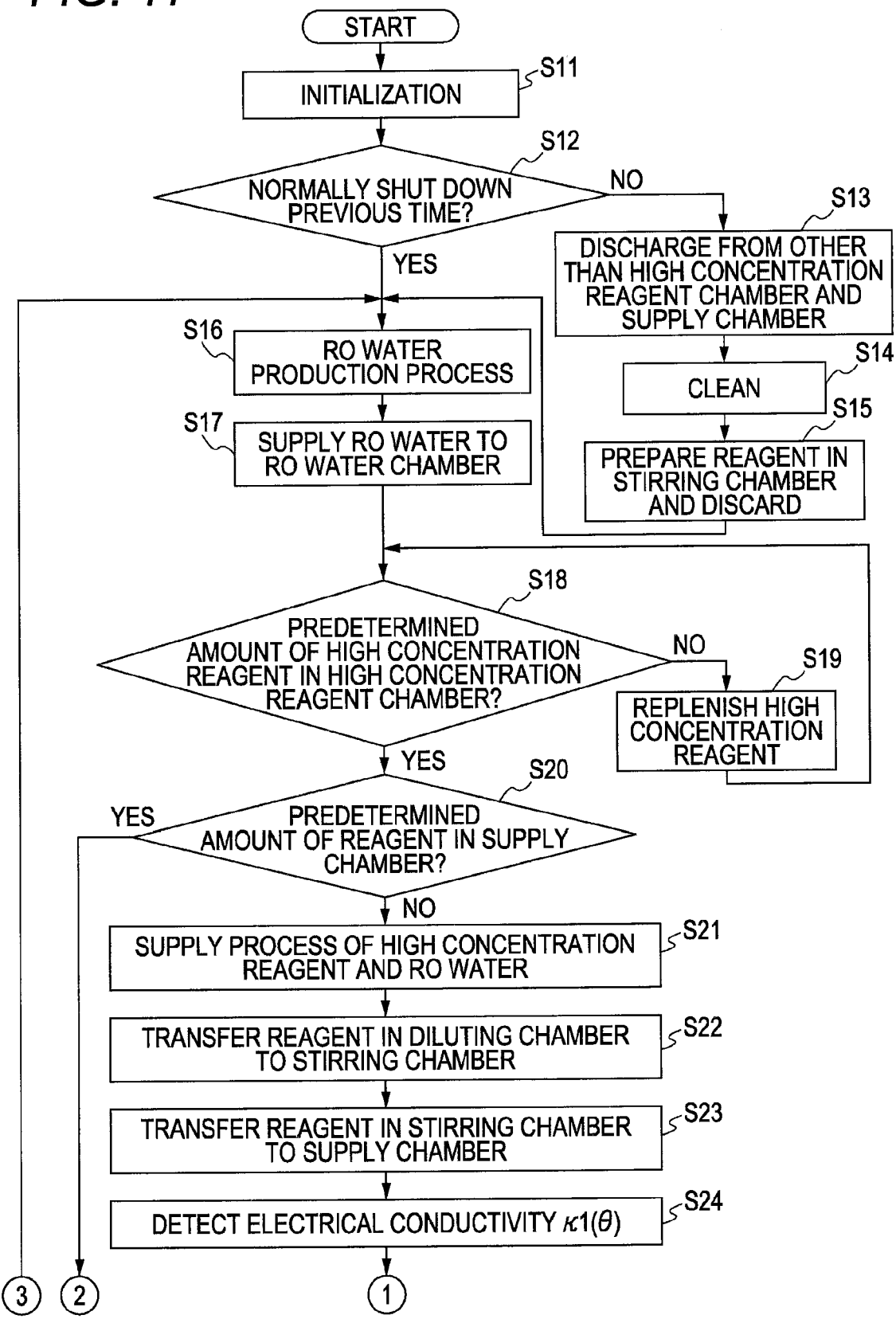
FIG. 11 is a flowchart explaining the reagent preparation processing operation of the reagent preparing device according to the first embodiment of the present invention.
Figure 12:
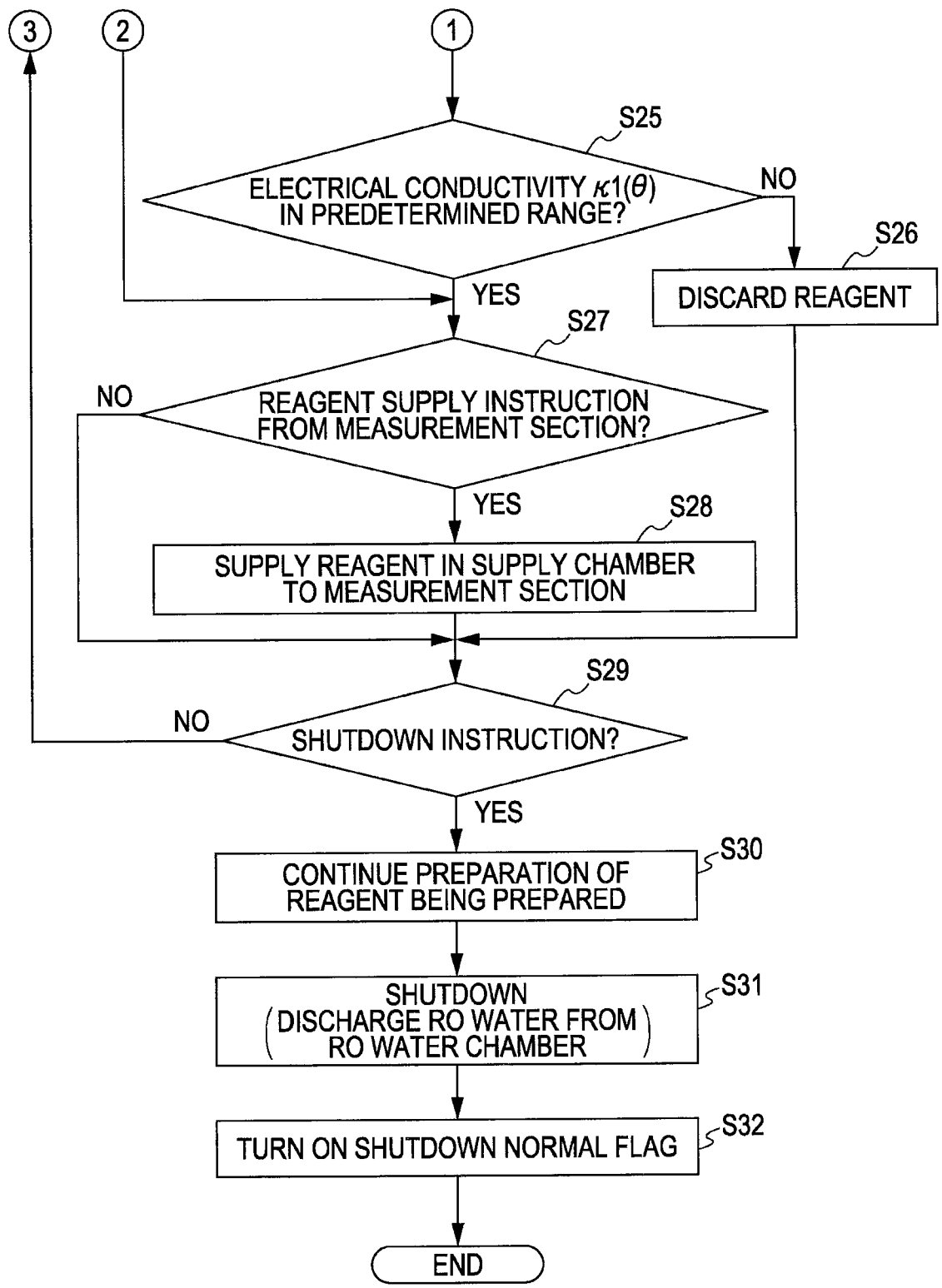
FIG. 12 is a flowchart explaining the reagent preparation processing operation of the reagent preparing device according to the first embodiment of the present invention.
Figure 13:
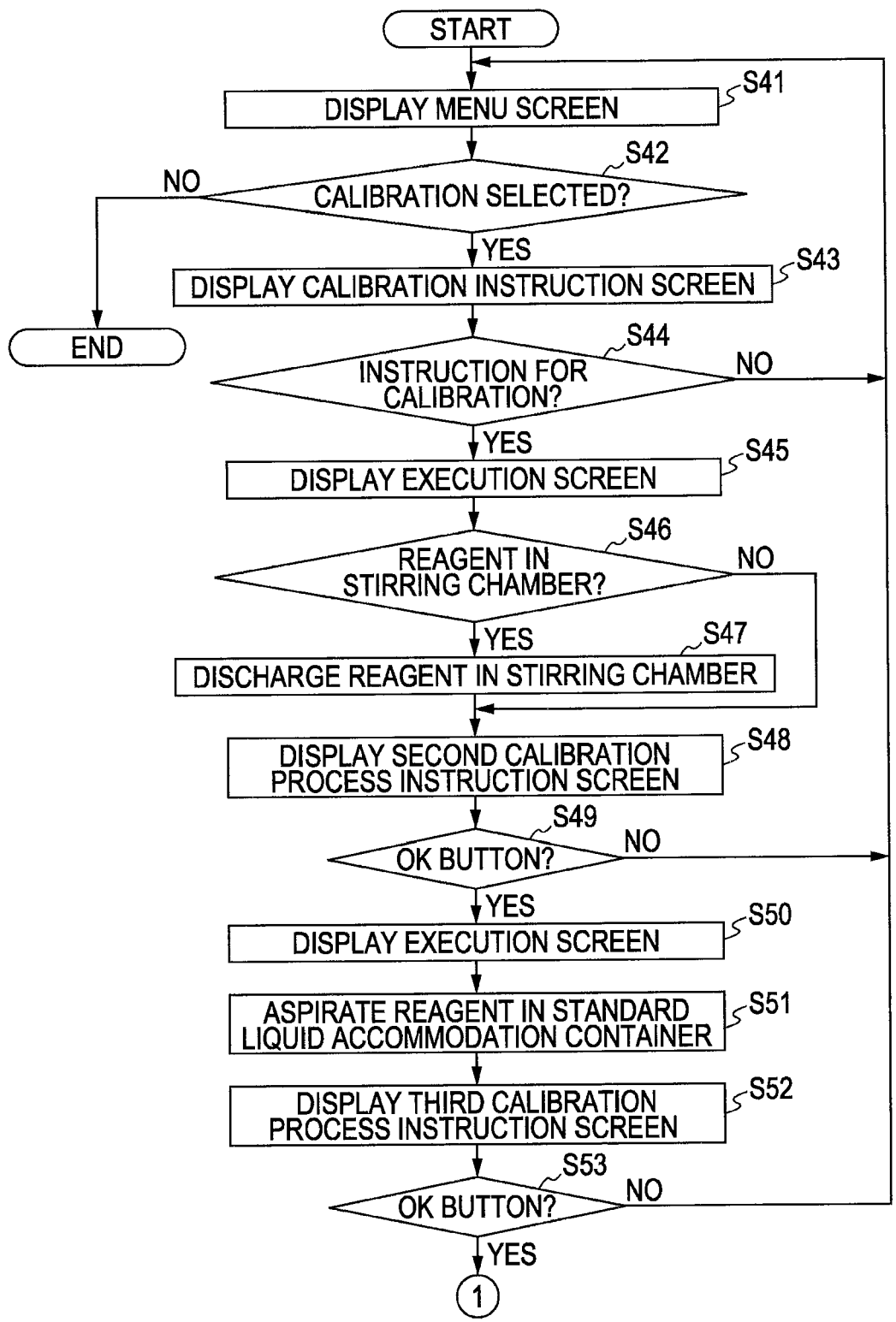
FIG. 13 is a flowchart describing the calibration process of the electrical conductivity meter of the reagent preparing device according to the first embodiment shown in FIG. 1.
Figure 14:
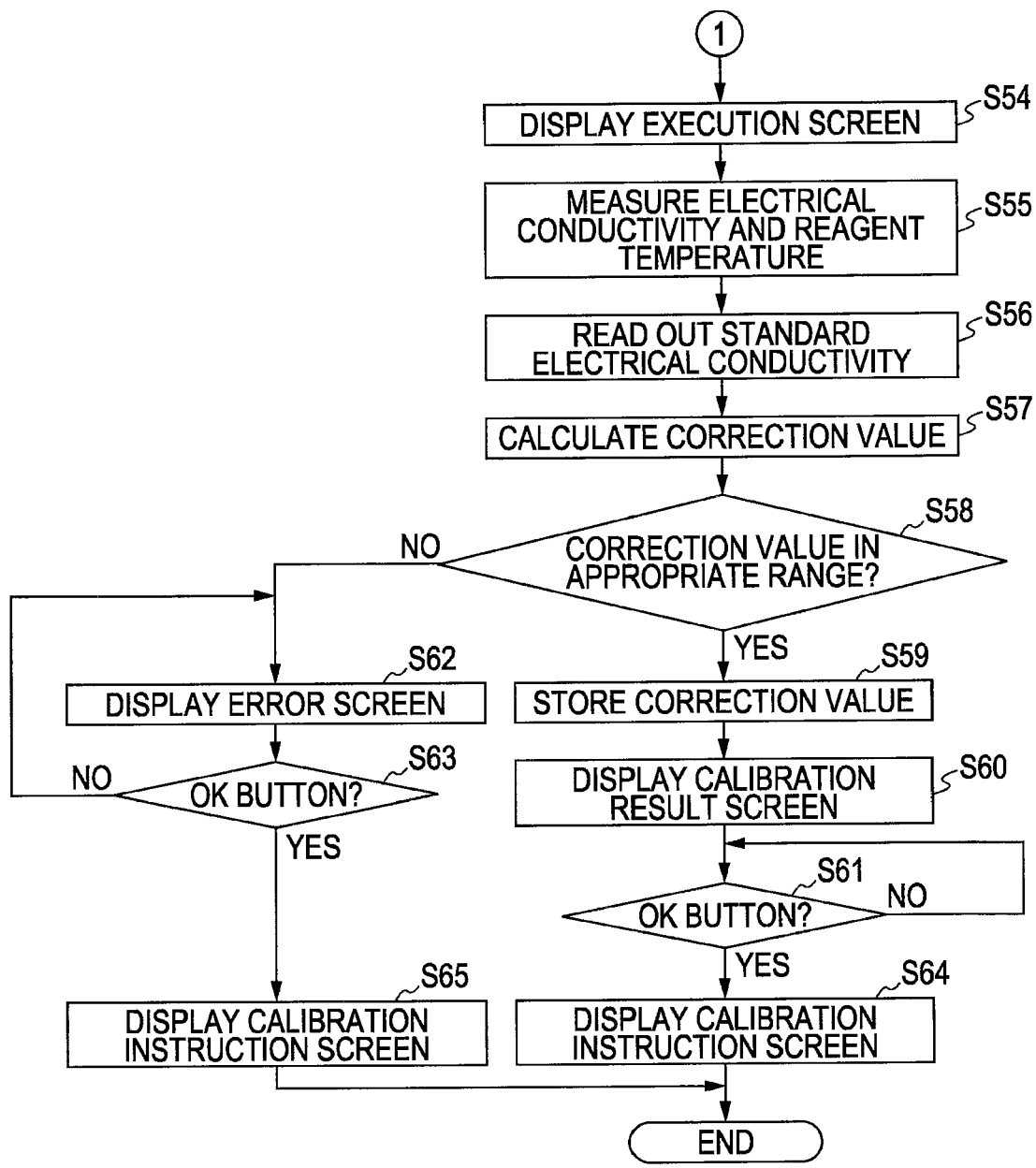
FIG. 14 is a flowchart describing the calibration process of the electrical conductivity meter of the reagent preparing device according to the first embodiment shown in FIG. 1.
Figure 15:
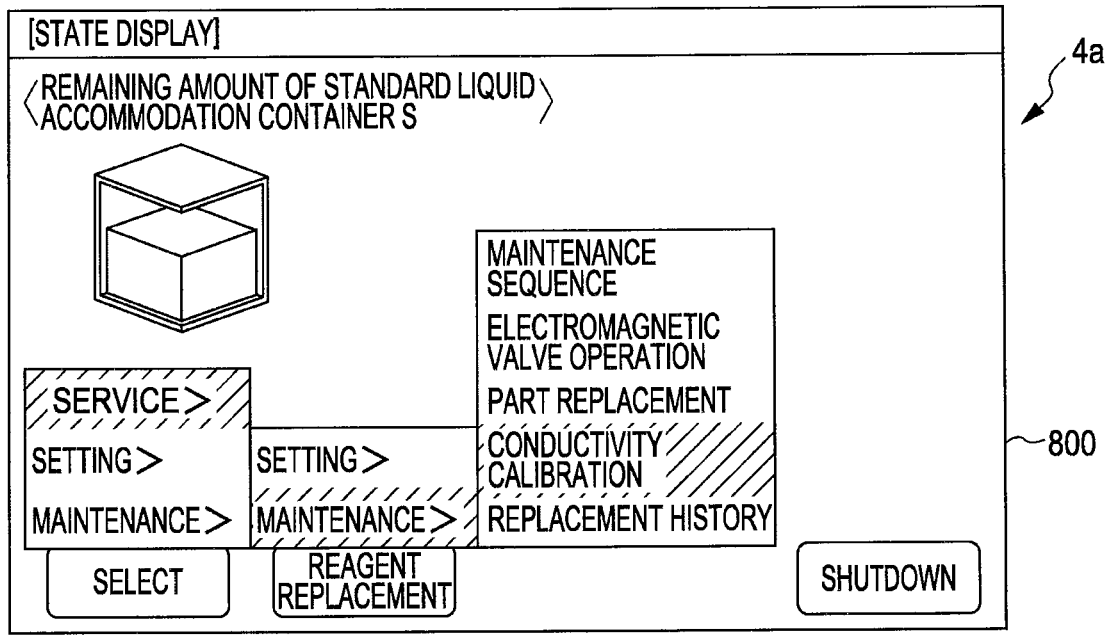
FIG. 15 is a view describing the transition of the screen displayed in the calibration process on the display unit of the reagent preparing device according to the first embodiment.

After the RO water production processing operation of step S16 of FIG. 11 is terminated, the RO water is supplied to the RO water chamber 42 in step S17. In step S18, whether or not a predetermined amount of high concentration reagent is accommodated in the high concentration reagent chamber 41 is determined based on the detection result of the float switch 100 by the CPU 49a. If the predetermined amount of high concentration reagent is not stored, the high concentration reagent is replenished to the high concentration reagent chamber 41 from the high concentration reagent tank 5 in step S19. Specifically, the electromagnetic valves 200 and 201 are opened with the electromagnetic valves 202 and 203 closed by the CPU 49a, so that the high concentration reagent is supplied to the high concentration reagent chamber 41 with the negative pressure force.

If the predetermined amount of high concentration reagent is accommodated in the high concentration reagent chamber 41, whether or not the predetermined amount of reagent is stored in the supply chamber 47 is determined by the CPU 49a. In other words, whether or not the reagent of greater than or equal to about 300 mL and less than or equal to about 600 mL is stored in the supply chamber 47 is determined. The process proceeds to step S27 if the predetermined amount of reagent is stored. If the predetermined amount of reagent is not stored, the supply process of the high concentration reagent and the RO water is performed in step S21.

In other words, about 300 mL of mixed solution of RO water and high concentration reagent is supplied to the diluting chamber 43 by supplying about 288 mL of RO water and about 12 mL of high concentration reagent to the diluting chamber 43 while being quantified by the diaphragm pumps 45a and 45b. The mixed solution can be supplied to the diluting chamber 44 by switching the drive of the electromagnetic valves 209 and 210.

After the supply process of the high concentration reagent and the RO water is performed by step S21 of FIG. 11, the electromagnetic valves 211 (212) and 217 are opened by the CPU 49a to transfer the reagent in the diluting chamber 43 (44) to the stirring chamber 46 with the negative pressure force in step S22. In this case, the transferred reagent is flowed along the inner wall of the stirring chamber 46 by the pipe 461 arranged in the stirring chamber 46 so as to be stirred in the stirring chamber 46.

In step S23, the electromagnetic valves 218 and 219 are opened after the electromagnetic valves 211 (212) and 217 are closed, and the reagent is transferred from the stirring chamber 46 to the supply chamber 47. In this case, in step S24, the electrical conductivity $\kappa1(\theta)$ is measured based on equation (14) by the electrical conductivity meter including the electrical conductivity acquiring unit 402 and the control unit 49, and the temperature θ of the reagent is measured by the thermometer including the electrical conductivity acquiring unit 402 and the control unit 49. Here, κ1(θ) is corrected based on the temperature θ. The electrical conductivity κ1(θ) indicates the true electrical conductivity of the reagent when calibration of the electrical conductivity meter is appropriately performed. In step S25, whether or not the temperature corrected electrical conductivity κ1(θ) or the supply control value is within a predetermined range is determined by the CPU 49a. Specifically, whether or not the measured electrical conductivity κ1(θ) is within a predetermined range with respect to the target value Z of the electrical conductivity at the diluting magnification of 25 times calculated by equation (2) is determined. If the electrical conductivity κ1(θ) is not within a predetermined range, the electromagnetic valve 219 is closed, the electromagnetic valve 221 is opened, and the reagent which electrical conductivity κ1(θ) is not within the predetermined range is discarded through the discarding flow path in step S26. Only the reagent diluted at satisfactory accuracy thus can be stored in the supply chamber 47.

In step S27, whether or not the reagent supply instruction from the measurement section 2 transmitted through the data processing section 3 is made is determined by the CPU 49a, and the process proceeds to step S29 if instruction is not made. If the reagent supply instruction is made, the reagent in the supply chamber 47 is transferred to the measurement section 2 through the filter 471 by the negative pressure force supplied from the measurement section 2 in step S28. In step S29, the presence of shutdown instruction from the user is determined by the CPU 49a, and the process proceeds to step S16 if the instruction is not made.

If the shutdown instruction is made, the above operation is continued until the reagent in the middle of the preparation is ultimately transferred to the supply chamber 47 in step S30. Specifically, if a predetermined amount (greater than or equal to about 300 mL and less than or equal to about 600 mL) of reagent is not in the supply chamber 47, the reagent diluted to a concentration different from the desired concentration remains in the flow path, the diluting chamber 43 (44), and the stirring chamber 46 when the operation is stopped in the middle of the preparation since the reagent preparation is continued through the operations of steps S21 to S26. Thus, the reagent diluted to a concentration different from the desired concentration is prevented from remaining in the flow path, the diluting chamber 43 (44), and the stirring chamber 46 by continuing the preparation operation in step S30.

In step S31, the shutdown is executed. In this case, the RO water is discharged from the RO water chamber 42. The RO water is thus prevented from being accumulated in the RO water chamber 42 until the reagent preparing device 4 is activated at the next time. Thereafter, in step S32, the flag indicating that the shutdown has been normally performed is set to ON, and the reagent preparation processing operation is terminated.

The calibration process of the electrical conductivity meter of the reagent preparing device 4 according to the first embodiment of the present invention will be described below with reference to FIGS. 13 to 24.

The calibration process starts when the user executes the display instruction of the menu screen 800. When the calibration process starts, the CPU 49a first displays the menu screen 800 (see FIG. 15) on the display unit 4a in step S41.

Figure 16:
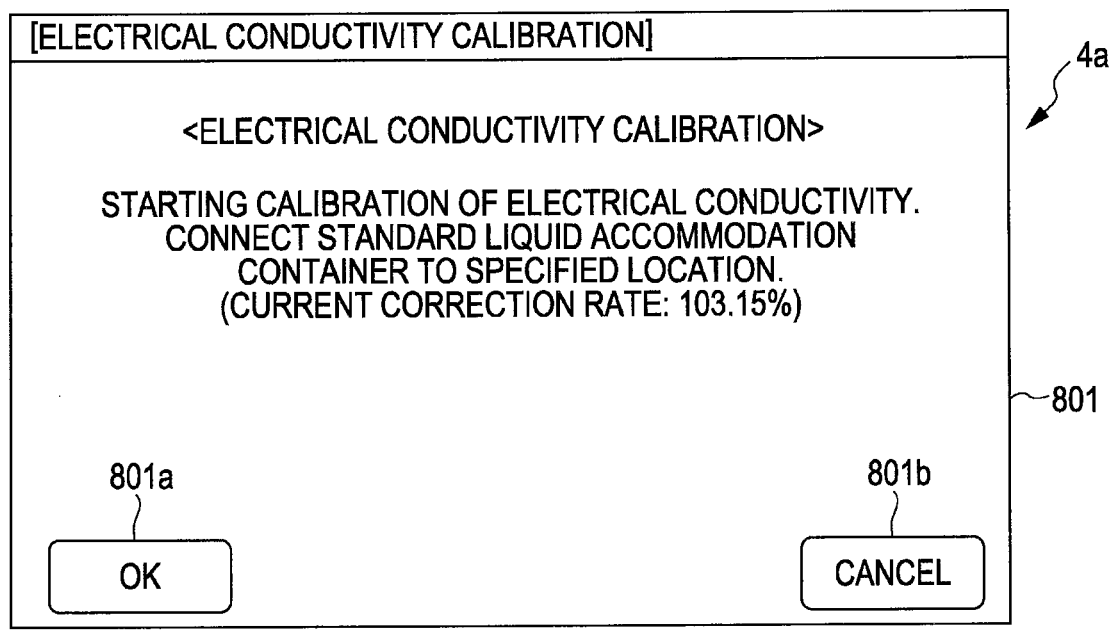
FIG. 16 is a view describing the transition of the screen displayed in the calibration process on the display unit of the reagent preparing device according to the first embodiment.
Figure 17:
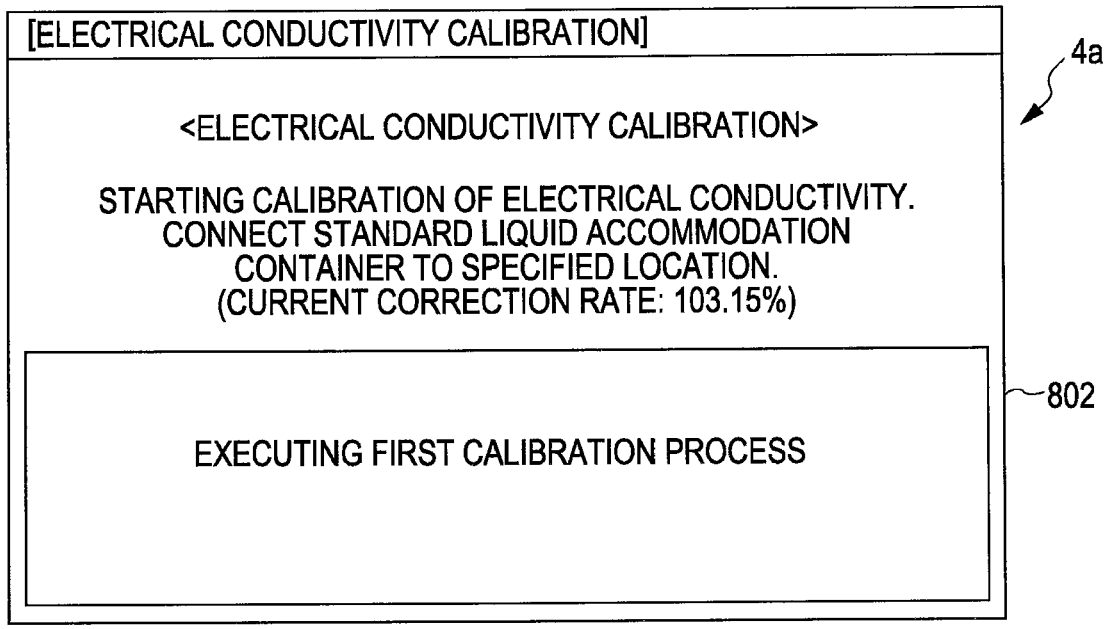
FIG. 17 is a view describing the transition of the screen displayed in the calibration process on the display unit of the reagent preparing device according to the first embodiment.
Figure 18:
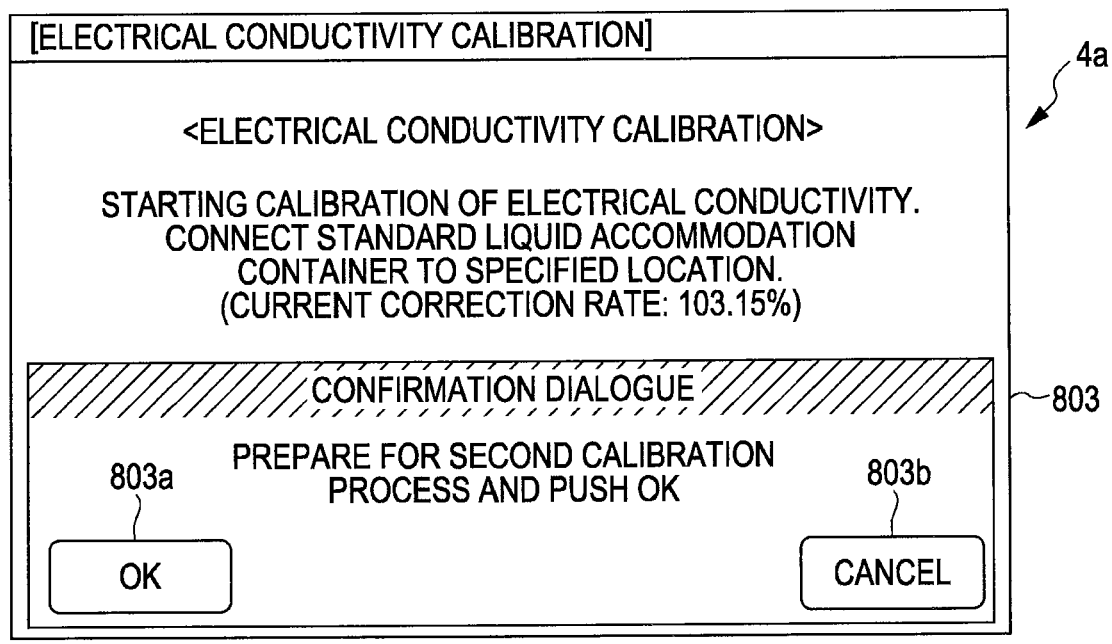
FIG. 18 is a view describing the transition of the screen displayed in the calibration process on the display unit of the reagent preparing device according to the first embodiment.
Figure 19:
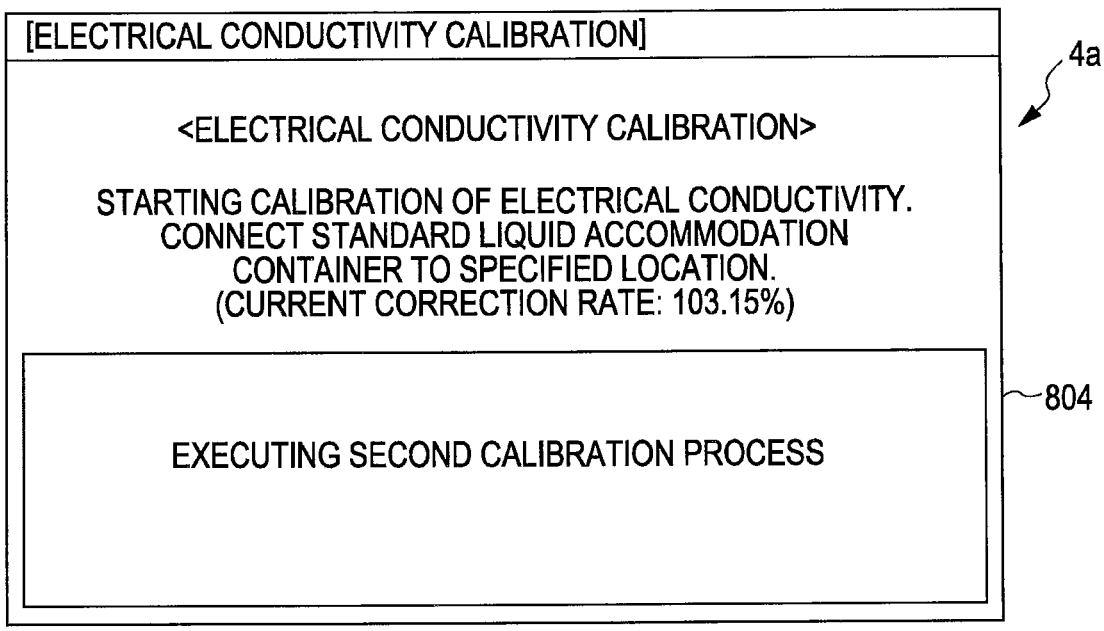
FIG. 19 is a view describing the transition of the screen displayed in the calibration process on the display unit of the reagent preparing device according to the first embodiment.
Figure 20:
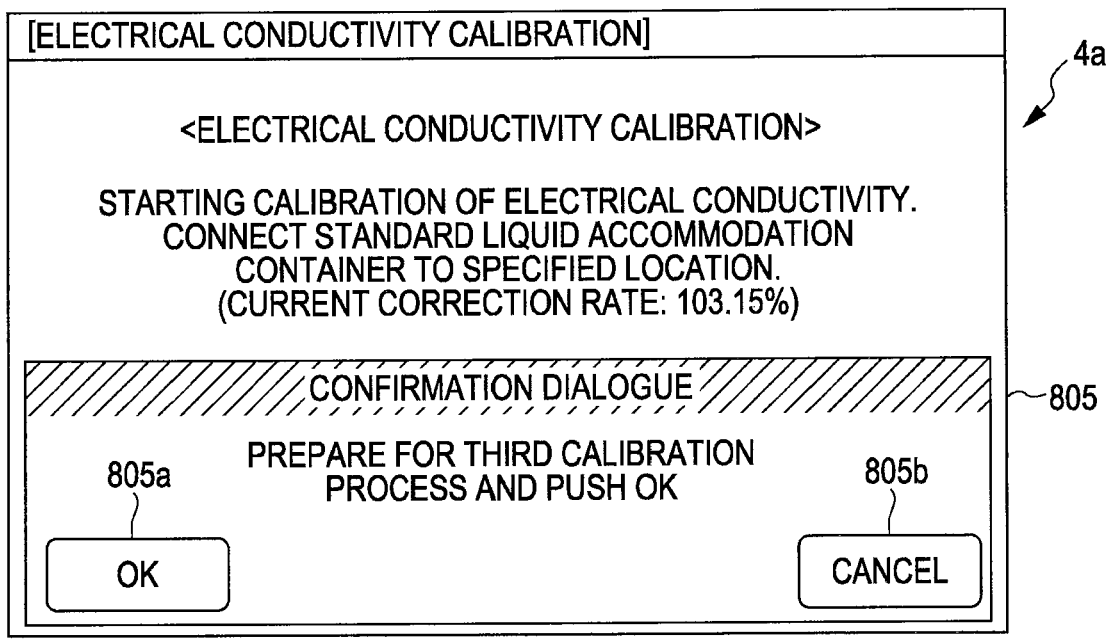
FIG. 20 is a view describing the transition of the screen displayed in the calibration process on the display unit of the reagent preparing device according to the first embodiment.
Figure 21:
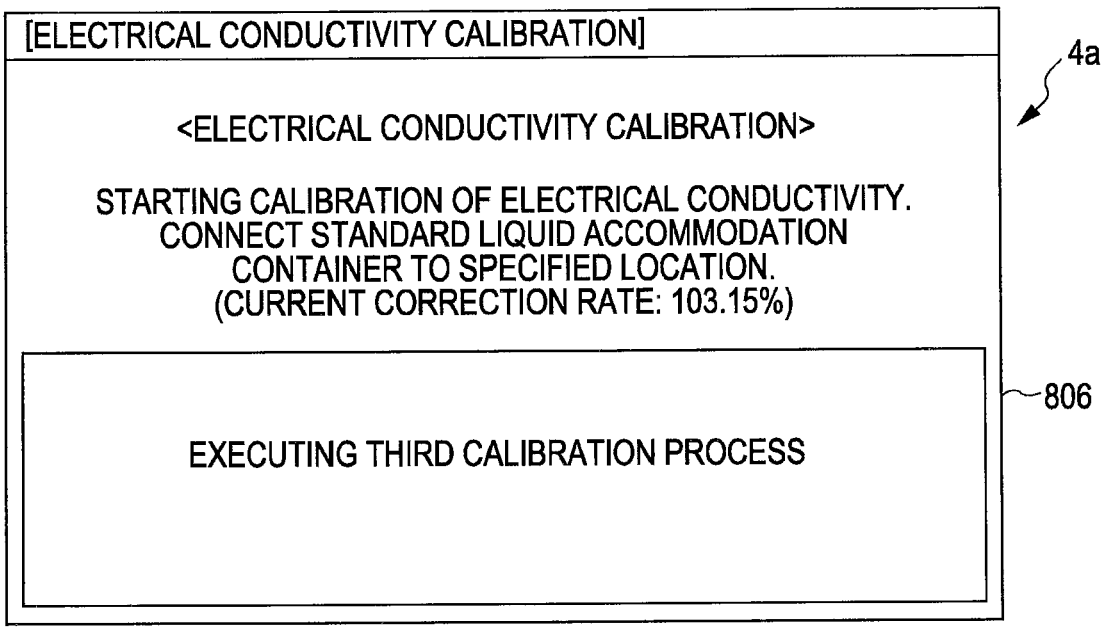
FIG. 21 is a view describing the transition of the screen displayed in the calibration process on the display unit of the reagent preparing device according to the first embodiment.
Figure 22:
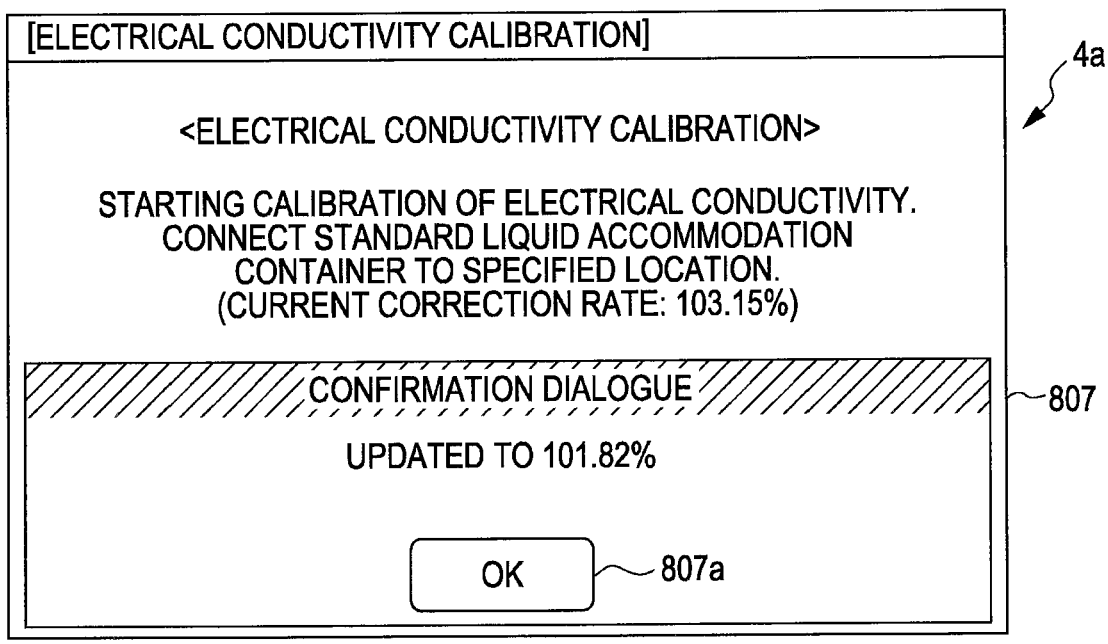
FIG. 22 is a view describing the transition of the screen displayed in the calibration process on the display unit of the reagent preparing device according to the first embodiment.
Figure 23:
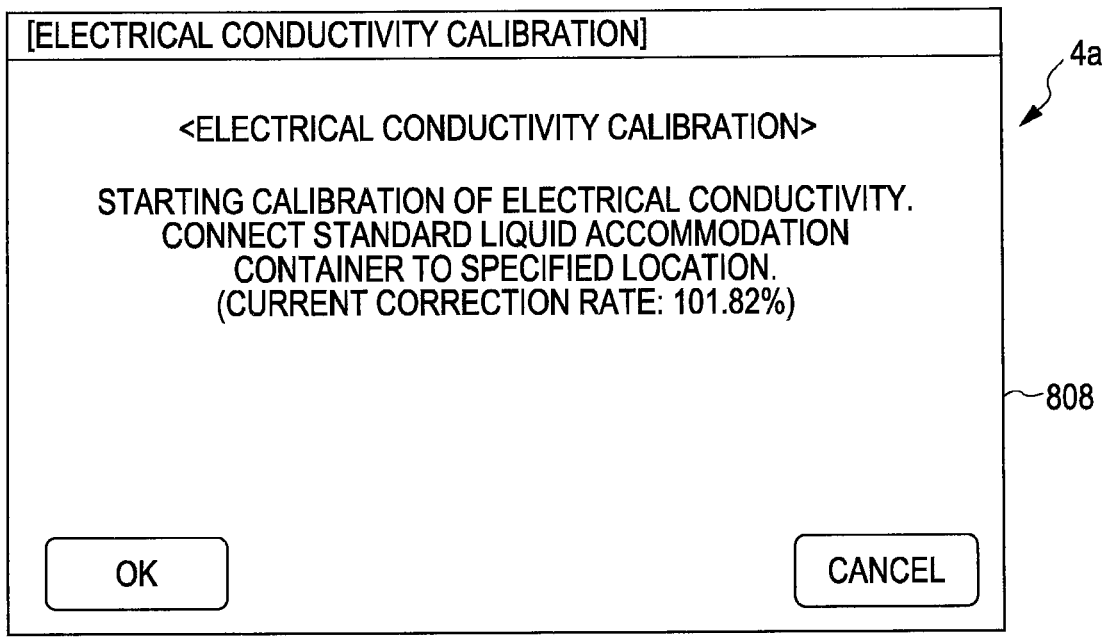
FIG. 23 is a view describing the transition of the screen displayed in the calibration process on the display unit of the reagent preparing device according to the first embodiment.
Figure 24:
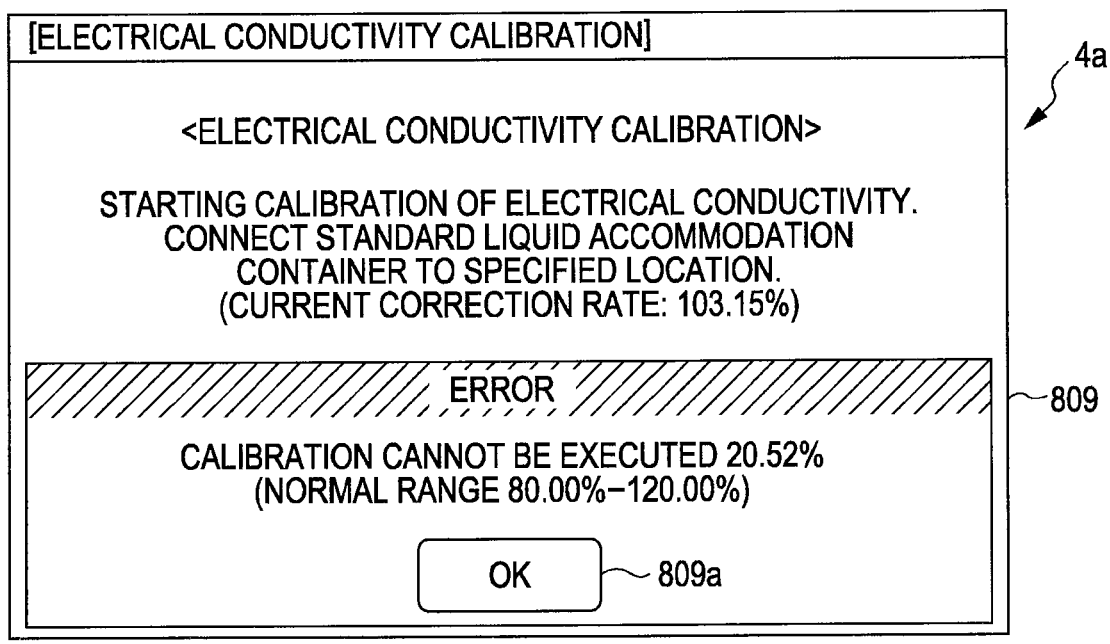
FIG. 24 is a view describing the transition of the screen displayed in the calibration process on the display unit of the reagent preparing device according to the first embodiment.

When calibrating the electrical conductivity meter, the user makes an instruction to calibrate the electrical conductivity meter to the reagent preparing device 4 by the touch panel type display unit 4a of the reagent preparing device 4. Specifically, "conductivity calibration" is selected on the menu screen 800 (see FIG. 15) displayed on the display unit 4a. In step S42, the CPU 49a determines whether or not "conductivity calibration" of the menu screen 800 is selected. If "conductivity calibration" is not selected, the calibration process is terminated. If "conductivity calibration" is selected, the CPU 49a displays a calibration instruction screen 801 on the display unit 4a, as shown in FIG. 16, in step S43.

The user pushes the OK button 801a of the calibration instruction screen 801 when performing the calibration of the electrical conductivity meter, and pushes the cancel button 801b of the calibration instruction screen 801 when not performing the calibration of the electrical conductivity meter. In step S44, the CPU 49a determines whether or not the calibration instruction is made. In other words, the CPU 49a determines that the calibration instruction is not made if the cancel button 801b is pushed, and displays the menu screen 800 on the display unit 4a. The CPU 49a determines that the calibration instruction is made if the OK button 801a is pushed, and starts the first calibration process. When the first calibration process starts, the CPU 49a displays an execution screen 802 (see FIG. 17) on the display unit 4a in step S45.

In the first calibration process, the CPU 49a determines whether or not the reagent is accommodated in the stirring chamber 46 in step S46. The CPU 49a proceeds to step S48 if the reagent is not accommodated in the stirring chamber 46. The CPU 49a discards all reagents in the stirring chamber 46 in step S47 if the reagent is accommodated in the stirring chamber 46. Specifically, the CPU 49a opens the electromagnetic valves 218 and 221 with the electromagnetic valves 211, 212, 217, and 219 closed to push out the mixed solution in the stirring chamber 46 to the discarding flow path with the positive pressure force.

After the discarding of the reagent in the stirring chamber 46 is terminated, the CPU 49a displays a second calibration process instruction screen 805 (see FIG. 18) on the display unit 4a in step S48.

When performing the second calibration process, the user removes the plug 462a at the distal end of the introducing path 462, connects the standard liquid accommodation container 500 with standard liquid to the introducing path 462, and pushes the OK button 803a of the second calibration process instruction screen 805. The user pushes the cancel button 803b of the second calibration process instruction screen 803 when not performing the calibration. In step S49, the CPU 49a determines whether or not the calibration instruction is made. In other words, the CPU 49a determines that the calibration instruction is not made if the cancel button 803b is pushed, and returns to step S41 to display the menu screen 800 on the display unit 4a. The CPU 49a determines that the execution instruction of the second calibration process is made if the OK button 803a is pushed, and starts the second calibration process. When the second calibration process starts, the CPU 49a displays an execution screen 804 (see FIG. 19) on the display unit 4a in step S50.

In the second calibration process, the CPU 49a introduces the reagent (standard liquid) in the standard liquid accommodation container 500 to the stirring chamber 46 in step S51. Specifically, the CPU 49a opens the electromagnetic valve 217 with the electromagnetic valves 211, 212, 218, 219, and 221 closed to aspirate the standard reagent (standard liquid) in the standard liquid accommodation container 500 to the stirring chamber 46 with the negative pressure force.

After the introduction of the standard liquid to the stirring chamber 46 is terminated, the CPU 49a displays a third calibration process instruction screen 805 (see FIG. 20) on the display unit 4a in step S52.

When performing the third calibration process, the user detaches the standard liquid accommodation container 500 from the introducing path 462, closes the plug 462a at the distal end of the introducing path 462, and pushes the OK button 805a of the third calibration process instruction screen 805. The user pushes the cancel button 805b of the third calibration process instruction screen 805 when not performing the calibration. In step S53, the CPU 49a determines whether or not the execution instruction of the third calibration process is made. In other words, the CPU 49a determines that the calibration instruction is not made if the cancel button 805b is pushed, and returns to step S41 to display the menu screen 800 on the display unit 4a. The CPU 49a determines that the execution instruction of the third calibration process is made if the OK button 805a is pushed, and starts the third calibration process. When the third calibration process starts, the CPU 49a displays an execution screen 806 (see FIG. 21) on the display unit 4a in step S54.

In the third calibration process, the CPU 49a acquires the electrical conductivity of the standard liquid in step S55. Specifically, the CPU 49a opens the electromagnetic valves 218 and 221 with the electromagnetic valves 211, 212, 217, and 219 closed to push out the standard liquid in the stirring chamber 46 to the discarding flow path with the positive pressure force. The standard liquid thereby flows through the electrical conductivity acquiring unit 402. The CPU 49a acquires the reference voltage Vin, the measurement voltage Vout, and the temperature $\theta$ of the reagent from the output of the A/D conversion circuits 412, 417, and 419 while the standard liquid flows through the electrical conductivity acquiring unit 402.

More specifically, after flowing the standard liquid for a predetermined time to clean the electrical conductivity acquiring unit 402, the CPU 49a measures the reference voltage Vin and the measurement voltage Vout ten times each. For the reference voltage Vin, the average of the measurement data for ten times is used to calculate the electrical conductivity. For the measurement voltage Vout, the data with the smallest value of the measurement data of ten times is used to calculate the electrical conductivity. The data with the smallest value of the measurement voltage Vout is used for the calculation due to the following reasons. In other words, air bubbles are sometimes mixed in the standard liquid being measured, where the resistance R (value of resistor 413 and resistor 414) of reagent becomes large, and the value of the measurement voltage Vout being measured becomes large by such amount. The measurement voltage Vout indicating the smallest value is assumed as the voltage in a state the mixture of air bubbles is the least, and thus the data with smallest value of the measurement data of ten times is used for the calculation with respect to the measurement voltage Vout. The data to be used in the calculation of the electrical conductivity is acquired in such manner. The electrical conductivity $\kappa(\theta)$ shown in equation (6) is calculated based on the acquired data. If the temperature $\theta$ of the reagent is not 25° C., the value is corrected to the value $\kappa(25)$ of the electrical conductivity when the temperature of the reagent is 25° C. using equations (7) and (8).

In step S56, the CPU 49a reads out the electrical conductivity (13.25 in the present embodiment) at 25° C. of the standard liquid stored in the ROM 49b.

In step S57, the CPU 49a calculates a new correction value P1 using equation (13) based on the electrical conductivity $\kappa(25)$ by measurement acquired in step S55 and the electrical conductivity (13.25) of the standard liquid read out from the ROM 49b.

In step S58, the CPU 49a determines whether or not the calculated correction value P1 is within a predetermined correction tolerable range ($0.8 \leq P1 \leq 1.2$). If the calculated correction value P1 is within the predetermined correction tolerable range, the CPU 49a stores the calculated correction value P1 in the memory of the control unit 49 in step S59, and displays a calibration result display screen 807 (see FIG. 22) on the display unit 4a in step S60. The CPU 49a determines whether or not the OK button 807a is pushed in the calibration result screen 807 in step S61, and proceeds to step S64 to display the calibration instruction screen 808 (see FIG. 23) of after the calibration if the OK button 807a is pushed. In the calibration instruction screen 808, the value of the correction value is different compared to the calibration instruction screen 801 (see FIG. 16) of before the calibration.

If calculated correction value P1 is outside the predetermined tolerable range, the CPU 49a displays a calibration error display screen 809 (see FIG. 24) on the display unit 4a in step S62. The CPU 49a determines whether or not the OK button 809a is pushed in the calibration error display screen 809 in step S63, and proceeds to step S65 to again display the calibration instruction screen 801 (see FIG. 16) of before the calibration if the OK button 809a is pushed. In the calibration instruction screen 801, the value of the correction value of before the calibration is displayed.

In the first embodiment, the electrical conductivity meter is calibrated based on the known electrical conductivity of the standard liquid and the electrical conductivity acquired by measuring the electrical conductivity of the standard liquid with the electrical conductivity meter, so that the calibration can be carried out such that the electrical conductivity meter shows a true value of the electrical conductivity of the reagent even when the electrical conductivity of the reagent is acquired by the electrical conductivity meter and the true value of the electrical conductivity of the reagent is not shown by the electrical conductivity meter (when value deviated from the true value is shown). Thus, the determination on whether or not the electrical conductivity of the reagent acquired by the electrical conductivity meter is within the tolerable range can be made using the true value of the electrical conductivity of the reagent. Therefore, the determination on whether or not to allow the supply of reagent to the measurement section 2 can be accurately made. In other words, only the reagent accurately determined that the true value of the electrical conductivity of the reagent is within the tolerable range can be supplied to the measurement section 2, and thus the reagent of low quality is suppressed from being supplied to the measurement section 2.

In the first embodiment, the electrical conductivity $\kappa 1(\kappa)$ of the reagent is acquired based on the electrical conductivity $\kappa(\theta)$ calculated using the reference voltage and the measurement voltage output from the electrical conductivity meter and the correction value P for correcting the electrical conductivity $\kappa(\theta)$, and the electrical conductivity meter is calibrated by changing the correction value P. With such configuration, the calibration can be carried out by changing the correction value P so that $\kappa 1(\theta)$ shows a true value based on the known electrical conductivity and the electrical conductivity acquired by measuring the electrical conductivity of the standard liquid by the electrical conductivity meter even if the electrical conductivity $\kappa 1(\theta)$ of the reagent acquired based on the electrical conductivity $\kappa(\theta)$ and the correction value P does not show a true value. Therefore, the true value of the electrical conductivity of the reagent can be acquired based on $\kappa(\theta)$ and the correction value P1 after the calibration.

In the first embodiment, the electrical conductivity of the reagent measured by the electrical conductivity meter and the concentration of the reagent have a predetermined relationship by determining the concentration of the reagent based on the electrical conductivity of the reagent, and thus the concentration of the reagent can be accurately determined based on the electrical conductivity of the reagent acquired by the electrical conductivity meter calibrated based on the known electrical conductivity. If the true value of the electrical conductivity of the reagent is within the tolerable range, such reagent can be accurately determined as having the desired concentration. Therefore, only the reagent accurately determined to have the desired concentration can be supplied to the measurement section 2, whereby the reagent having a concentration different from the desired concentration can be suppressed from being supplied to the measurement section 2.

In the first embodiment, the electrical conductivity is acquired based on the electrical conductivity $\kappa(\theta)$ calculated based on the data output from the electrical conductivity meter, the temperature $\theta$ of the reagent, and the correction value P. With such configuration, the electrical conductivity that takes into consideration temperature change can be acquired. The concentration of the reagent can be more accurately determined using the electrical conductivity that takes into consideration temperature change. The calibration can be more accurately performed since the calibration can be performed based on the electrical conductivity that takes into consideration temperature change.

In the first embodiment, the calculated correction value is assumed as the correction value of after the calibration if the calculated correction value P1 is within the correction tolerable range (0.8≤P2≤1.2), so that the calculated correction value can be assumed as the correction value of after the calibration assuming the calibration has been appropriately performed if the calculated correction value is within the correction tolerable range, and the calculated correction value is prevented from being the correction value of after the calibration if the calculated correction value is outside the correction tolerable range. Thus, the reagent of low quality is prevented from being supplied to the measurement section 2 when the electrical conductivity of the reagent is measured using the correction value of after the inappropriate calibration when inappropriate calibration is performed.

In the present embodiment, the correction value is not changed if the calculated correction value P1 is outside the correction tolerable range (P2<0.8, P2>1.2), and the user recognizes the failure of the calibration when notified that the correction value is not changed, and thus calibration can be performed again and the reagent preparing device 4 can be adjusted. Thus, the preparation of the reagent is suppressed from being carried out without the calibration being performed.

In the first embodiment, the reagent is discarded without being supplied to the supply chamber 47 when the calculated electrical conductivity is outside the tolerable range, and the reagent is discarded without being supplied to the reagent accommodation unit when the electrical conductivity of the reagent calibrated to indicate a true value is outside the tolerable range, and thus the reagent of low quality is suppressed from being supplied to the measurement section 2.

In the first embodiment, the reagent preparing device 4 performs the calibration when accepting the instruction for calibration at the touch panel type display unit 4a, so that calibration can be easily performed when desired by the user.

In the first embodiment, the liquid containing the same component as the component contained in the reagent at the same concentration is used as the standard liquid, so that the reagent preparing device 4 does not need to be cleaned after the calibration is finished even if the standard liquid is introduced into the reagent preparing device 4 when performing the calibration. The reagent thus can be prepared immediately after performing the calibration.

Second Embodiment

A second embodiment will now be described with reference to FIGS. 25 and 26. In the second embodiment, a reagent preparing device 600 in which the RO water producing unit 700 is arranged at the exterior, different from the first embodiment, will be described.

Figure 25:
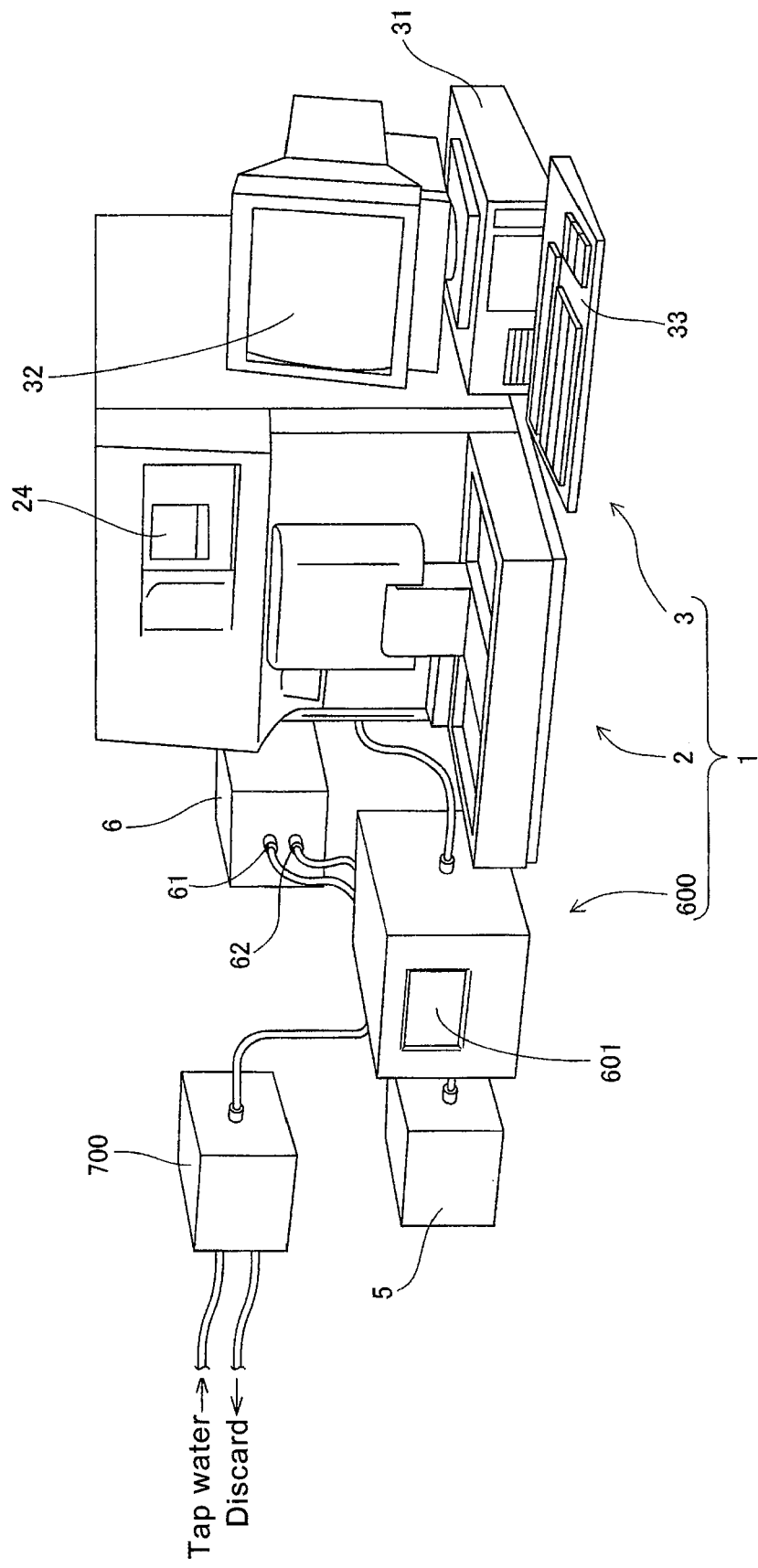
FIG. 25 is a perspective view showing a usage mode of a reagent preparing device according to a second embodiment of the present invention.

As shown in FIG. 25, the blood analyzer 1 is configured by the measurement section 22 having a function of measuring blood, the data processing section 3 for analyzing the measurement data output from the measurement section 22 and obtaining an analysis result, and the reagent preparing device 600 for preparing a reagent to be used in the processing of specimens.

Figure 26:
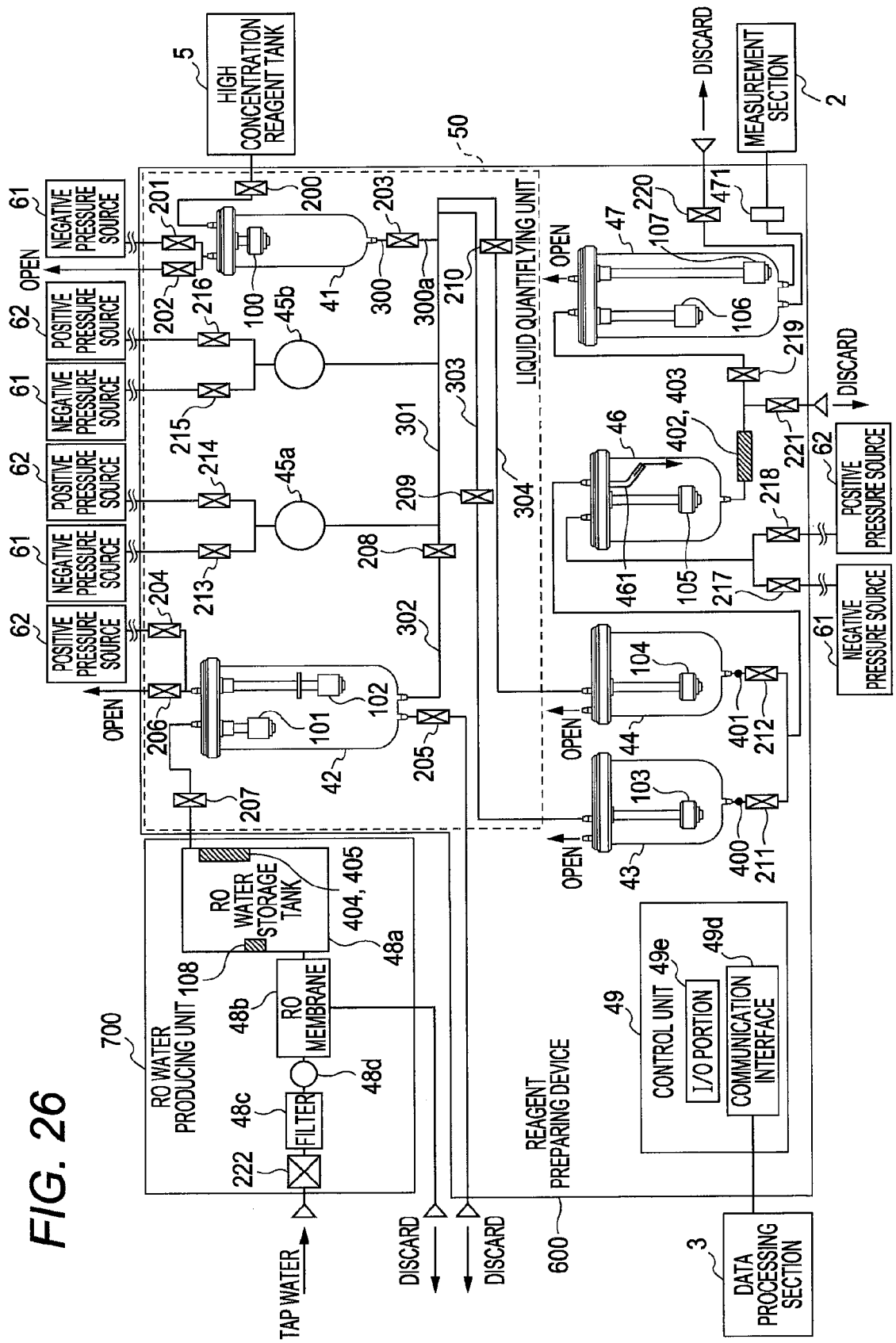
FIG. 26 is a block diagram showing a configuration of the reagent preparing device according to the second embodiment shown in FIG. 25.

As shown in FIGS. 25 and 26, in the second embodiment, the reagent preparing device 600 is configured to prepare the reagent to be used in blood analysis by diluting the high concentration reagent to a desired concentration using the RO water produced by the RO water producing unit 700 arranged at the exterior.

As shown in FIG. 25, the reagent preparing device 600 includes a touch panel type display unit 601. The CPU 49a of the reagent preparing device 600 is configured to accept instructions such as activation, shutdown, and various types of settings of the reagent preparing device 600 from the user through the touch panel type display unit 601.

Other structures of the second embodiment are similar to those of the first embodiment.

In the second embodiment, the configuration of the reagent preparing device 600 is simplified by arranging the RO water producing unit 700 at the exterior of the reagent preparing device 600.

Other effects of the second embodiment are similar to the first embodiment.

The embodiments disclosed herein are illustrative in all aspects and should not be construed as being exclusive. The scope of the present invention is defined by the Claims rather than by the description of the embodiments made above, and all modifications equivalent in meaning to the Claims and within the scope of the Claims are to be encompassed.

Figure 27:
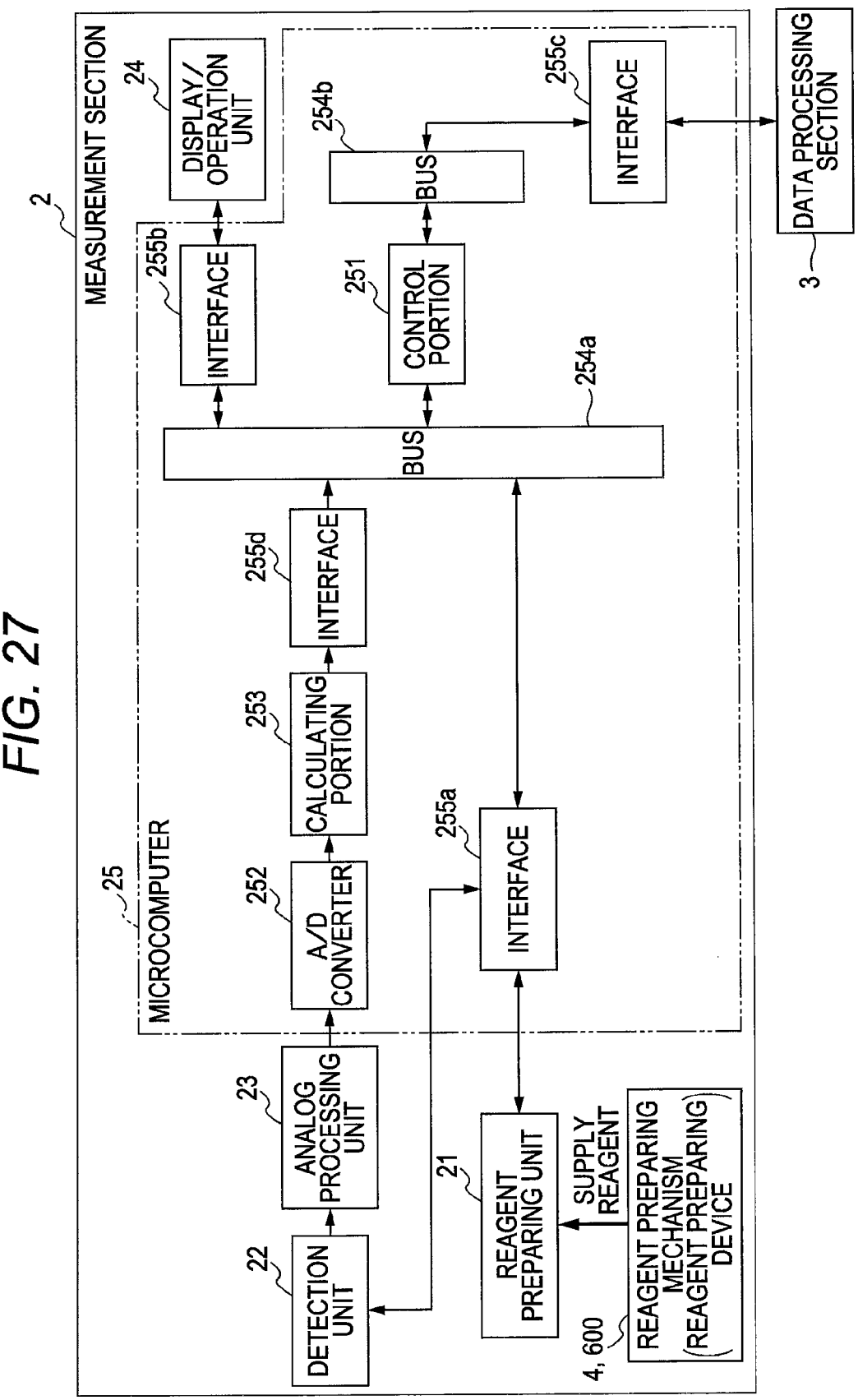
FIG. 27 is a block diagram explaining a variant of the reagent preparing device according to the first embodiment shown in FIG. 1 and the second embodiment shown in FIG. 25.

For instance, in the first embodiment and the second embodiment, the reagent preparing device installed separate from the measurement section 2 has been described as an example of the reagent preparing device, but the present invention is not limited thereto, and may be a reagent preparing device 4 (600) that is arranged in the measurement section 2 and that functions as a reagent preparation mechanism, as shown in FIG. 27. The measurement section 2 (device) including such reagent preparation mechanism includes blood cell counting device, immune measurement device, and smear producing device, but is particularly suited to the blood cell counting device in which the usage amount of the diluting liquid is large.

In the first and second embodiments, an example of measuring the electrical conductivity of the reagent to determine the concentration of the reagent has been described, but the present invention is not limited thereto, and other properties may be measured as long as the properties reflect the concentration of the reagent. For instance, since absorbance of the reagent is assumed to reflect the concentration of the reagent, the absorbance of the reagent may be measured. Furthermore, pH of the reagent may be measured.

In the first and second embodiments, an example in which the reagent preparing device 4 starts the calibration when the user makes an instruction for calibration by operating the display unit 4a has been described, but the present invention is not limited thereto, and the reagent preparing device may automatically perform the calibration. In this case, a timer for timing the elapsed time from the previous calibration is arranged in the reagent preparing device, and the calibration is automatically performed every time a predetermined time has elapsed. The calibration may be executed when a predetermined item of the analysis result of the blood analyzer 1 is outside a predetermined range. The predetermined item includes an item (e.g., MCV: Mean Corpuscular Volume) having great influence on the analysis result when the electrical conductivity is not calibrated. The analysis result used in the determination on whether outside the predetermined range may be an analysis result of the accuracy management sample, or an average value of the analysis result of a plurality of patient specimens. The determination on whether or not the analysis result is outside the predetermined range may be executed by the CPU 49a or may be executed by the CPU 31a. If executed by the CPU 31a, the CPU 31a notifies the CPU 49a that the analysis result is outside the predetermined range, and the CPU 49a that received the notification starts the calibration.

In the first and second embodiments, an example of measuring the temperature of the reagent using the thermistor 407 has been described, but the present invention is not limited thereto, and the temperature may be measured using a platinum resistance thermometer bulb or a thermocouple.

In the first and second embodiments, an example of calibrating the electrical conductivity acquiring unit by changing the correction value P has been described, but the present invention is not limited thereto, and the electrical conductivity acquiring unit may be calibrated by changing the magnitude of the output voltage of the AC voltage 408.

In the first and second embodiments, an example of supplying the reagent in the supply chamber 47 to the measurement section 2 by the negative pressure force supplied from the measurement section 2 has been described, but the present invention is not limited thereto, and the reagent may be supplied to the measurement section 2 by supplying the positive pressure force to the supply chamber 47.

In the first and second embodiments, the reagent preparing device configured to supply the prepared reagent to the blood analyzer 1 has been described, but the present invention is not limited thereto, and may be a reagent preparing device configured to supply the prepared reagent to a urine analyzer.

What is claimed is:

1. A reagent preparing device capable of supplying a predetermined reagent, which includes a first liquid and a second liquid different from the first liquid, to a measurement section for measuring a specimen using the reagent, comprising:
   a pressure generating unit for generating a pressure for transferring each liquid in the reagent preparing device;
   a diluting chamber for preparing the reagent by mixing the first liquid and the second liquid;
   a stirring chamber having an inlet for receiving the reagent prepared in the diluting chamber and an outlet for supplying the reagent accommodated therein to the measurement section by the pressure generated by the pressure generating unit;
   a standard container accommodating a standard liquid having a known electrical conductivity and connected to the stirring chamber through an introducing path;
   an electrical conductivity meter for measuring an electrical conductivity of the reagent or the standard liquid accommodated in the stirring chamber;
   a reagent discarding unit comprising a discarding flow path that is connected to the outlet of the stirring chamber for discarding the reagent accommodated in the stirring chamber, the electrical conductivity meter is disposed along the discarding flow path such that the electrical conductivity meter measures the conductivity of the reagent standard liquid being transferred from the stirring chamber to the discarding flow path; and
   a processor communicably connected to the reagent preparing device and programmed to:
   when preparing the reagent,
      receiving from the electrical conductivity meter a measurement result obtained by measuring the conductivity of the reagent accommodated in the stirring chamber; and
      controlling the chamber and the pressure generating unit to supply the reagent accommodated in the chamber to the measurement section according to the measurement result of the reagent received from the electrical conductivity meter, and
   when calibrating the electrical conductivity meter, controlling the reagent discarding unit to discard the reagent accommodated in the stirring chamber;
      controlling the pressure generating unit to introduce the standard liquid from the standard liquid container to the chamber through the introducing path;
      receiving from the electrical conductivity meter a measurement result obtained by measuring a conductivity of the standard liquid accommodated in the stirring chamber; and
      calibrating the electrical conductivity meter based on a known conductivity value of the standard liquid and the measurement result of the standard liquid received from the electrical conductivity meter.

2. The reagent preparing device according to claim 1, wherein the processor controls the chamber and the pressure generating unit to supply the reagent accommodated in the chamber to the measurement section based on a supply control value, the supply control value being based on a first measurement value output from the characteristic measurement device and a correction value for correcting the first measurement value; and the characteristic measurement device is calibrated by changing the correction value.

3. The reagent preparing device according to claim 1, further comprising:
   a thermometer for measuring a temperature of the reagent;
   wherein the processor controls the chamber and the pressure generating unit to supply the reagent accommodated in the chamber to the measurement section based on the supply control value based on the first measurement value output from the electrical conductivity meter, a second measurement value output from the thermometer, and the correction value.

4. The reagent preparing device according to claim 2, wherein
   when calibrating the characteristic measurement device, the processor calculates a temporary correction value based on the known characteristic value of the standard liquid and the measurement result obtained by measuring the characteristic of the standard liquid accommodated in the chamber by the characteristic measurement device, and sets the temporary correction value as the correction value when the temporary correction value is within a predetermined correction tolerable range.

5. The reagent preparing device according to claim 4, wherein the processor does not set the temporary correction value as the correction value when the temporary correction value is outside the predetermined correction tolerable range, and notifies a user that the correction value has not been changed.

6. The reagent preparing device according to claim 1, wherein
the processor controls the reagent discarding unit to discard the reagent accommodated in the chamber when the measurement result of the reagent by the characteristic measurement device is outside a predetermined range.

7. The reagent preparing device according to claim 1, wherein the standard liquid contains a component same as a component contained in appropriately prepared the predetermined reagent at a same concentration.

8. The reagent preparing device according to claim 1, wherein the processor comprises a memory for storing the known characteristic value of the standard liquid.

9. The reagent preparing device according to claim 2, wherein
the processor comprises a memory for storing the correction value; and
the characteristic measurement device is calibrated by rewriting the correction value stored in the memory.

10. The reagent preparing device according to claim 1, wherein the processor is communicably connected to a computer for acquiring a measurement result by the measurement section, and calibrates the characteristic measurement device when receiving a predetermined notification from the computer.

11. A specimen processing system comprising:
a measurement section for measuring a specimen using a predetermined reagent including a first liquid and a second liquid different from the first liquid;
a pressure generating unit for generating a pressure for transferring each liquid;
a diluting chamber for preparing the reagent by mixing the first liquid and the second liquid;
a stirring chamber having an inlet for receiving the reagent prepared in the diluting chamber and an outlet for supplying the reagent accommodated therein to the measurement section by the pressure generated by the pressure generating unit;
a standard container accommodating a standard liquid having a known electrical conductivity and connected to the stirring chamber through an introducing path;
an electrical conductivity meter for measuring an electrical conductivity of the reagent or the standard liquid accommodated in the stirring chamber;
a reagent discarding unit comprising a discarding flow path that is connected to the outlet of the stirring chamber for discarding the reagent accommodated in the stirring chamber, the electrical conductivity meter is disposed along the discarding flow path such that the electrical conductivity meter measures the conductivity of the reagent standard liquid being transferred from the stirring chamber to the discarding flow path; and
a processor communicably connected to the reagent preparing device and programmed to:
when preparing the reagent,
receiving from the electrical conductivity meter a measurement result obtained by measuring the conductivity of the reagent accommodated in the stirring chamber; and
controlling the chamber and the pressure generating unit to supply the reagent accommodated in the chamber to the measurement section according to the measurement result of the reagent received from the electrical conductivity meter, and
when calibrating the electrical conductivity meter, controlling the reagent discarding unit to discard the reagent accommodated in the stirring chamber;
controlling the pressure generating unit to introduce the standard liquid from the standard liquid container to the chamber through the introducing path;
receiving from the electrical conductivity meter a measurement result obtained by measuring a conductivity of the standard liquid accommodated in the stirring chamber; and
calibrating the electrical conductivity meter based on a known conductivity value of the standard liquid and the measurement result of the standard liquid received from the electrical conductivity meter.

12. The specimen processing system according to claim 11, wherein the processor automatically starts the calibration of the characteristic measurement device when a predetermined condition is met.

13. The specimen processing system according to claim 12, further comprising:
a timer for measuring an elapsed time from a previous calibration; wherein the processor automatically starts the calibration when the elapsed time measured by the timer reaches a predetermined time.

14. The specimen processing system according to claim 12, wherein the processor automatically starts the calibration when the measurement result of the measurement section matches a predetermined condition.

15. The specimen processing system according to claim 11, wherein the processor controls the chamber and the pressure generating unit to supply the reagent accommodated in the chamber to the measurement section based on a supply control value, the supply control value being based on a first measurement value output from the characteristic measurement device and a correction value for correcting the first measurement value; and
the characteristic measurement device is calibrated by changing the correction value.

16. The specimen processing system according to claim 11, further comprising:
a thermometer for measuring a temperature of the reagent; wherein
the processor controls the chamber and the pressure generating unit to supply the reagent accommodated in the chamber to the measurement section based on the supply control value based on the first measurement value output from the electrical conductivity meter, a second measurement value output from the thermometer, and the correction value.

* * * * *